US006060042A

United States Patent [19]

[11] Patent Number: 6,060,042

Schuhmacher et al.

[45] Date of Patent: May 9, 2000

[54] USE OF CHOLESTERIC, LIQUID-CRYSTALLINE COMPOSITIONS AS UV FILTERS IN COSMETIC AND PHARMACEUTICAL PREPARATIONS

[75] Inventors: Peter Schuhmacher, Mannheim; Norbert Schneider, Altrip; Horst Westenfelder, Neustadt; Sylke Haremza, Neckargemünd; Thorsten Habeck, Meckenheim; Frank Meyer, Heidelberg, all of Germany

[73] Assignee: BASF Aktiengesellschaft, Ludwigshafen, Germany

[21] Appl. No.: 09/324,712

[22] Filed: Jun. 3, 1999

[30] Foreign Application Priority Data

Jun. 4, 1998 [DE] Germany ........................... 198 24 972

[51] Int. Cl.$^7$ ............................... A61K 7/42; A61K 7/44; A61K 7/00

[52] U.S. Cl. .............................................. 424/60; 400/401

[58] Field of Search ............................... 424/59, 60, 400, 424/401

[56] References Cited

U.S. PATENT DOCUMENTS

| | | | |
|---|---|---|---|
| 5,744,057 | 4/1998 | Meyer et al. | 252/299 |
| 5,780,629 | 7/1998 | Etzbach et al. | 544/296 |
| 5,827,449 | 10/1998 | Hanelt et al. | 252/299 |
| 5,833,880 | 11/1998 | Siemensmeyer et al. | 252/299 |
| 5,851,277 | 12/1998 | Mueller-Rees et al. | 106/287 |

FOREIGN PATENT DOCUMENTS

| | | |
|---|---|---|
| 750029 | 12/1996 | European Pat. Off. . |
| 4342280 | 6/1995 | Germany . |
| 4408171 | 9/1995 | Germany . |
| 19532408 | 3/1997 | Germany . |
| 19629761 | 6/1997 | Germany . |
| 19611101 | 9/1997 | Germany . |
| 19619460 | 11/1997 | Germany . |
| 19638797 | 3/1998 | Germany . |
| 19738369 | 3/1999 | Germany . |
| 95/16007 | 6/1995 | WIPO . |

*Primary Examiner*—Shelley A. Dodson
*Attorney, Agent, or Firm*—Keil & Weinkauf

[57] ABSTRACT

The use of cholesteric, liquid-crystalline compositions comprising a) at least one chiral, liquid-crystalline, polymerizable monomer of the formula I, $$[Z^1\text{-}Y^1\text{-}(A^1)_m\text{-}Y^2\text{-}M^1\text{-}Y^3\text{-}]_n\text{-}X \qquad \text{I}$$

by means of which a cholesteric, liquid-crystalline phase with a pitch of less than 450 nm can be obtained, or b) a mixture of $b_1$) at least one achiral, liquid-crystalline, polymerizable monomer of the formula II $$Z^2\text{-}Y^4\text{-}(A^2)\text{-}_o\text{-}Y^5\text{-}M^2\text{-}Y^6\text{-}(A^3)_p\text{-}Y^7\text{-}Z^3 \qquad \text{II}$$

and $b_2$) at least one chiral additive by means of which a cholesteric, liquid-crystalline phase with a pitch of less than 450 nm can be obtained, where the variables are as defined in the description, as UV filters in cosmetic and pharmaceutical preparations for protecting the human skin or human hair against sunlight, alone or together with UV-absorbent compounds which are known per se for cosmetic and pharmaceutical preparations.

12 Claims, No Drawings

USE OF CHOLESTERIC, LIQUID-CRYSTALLINE COMPOSITIONS AS UV FILTERS IN COSMETIC AND PHARMACEUTICAL PREPARATIONS

The present invention relates to the use of cholesteric, liquid-crystalline compositions as photostable UV filters in cosmetic and pharmaceutical preparations for protecting the human epidermis or human hair against UW radiation, especially in the range from 280 to 450 nm.

The light protection products used in cosmetic pharmaceutical preparations have the job of eliminating or at least reducing harmful effects of sunlight on the human skin. In addition, however, these light protection products also serve to protect other ingredients against destruction or degradation by UV radiation. In hair-cosmetic formulations, the aim is to reduce damage to keratin fibers by UV rays.

The sunlight reaching the earth's surface has a UV-B component (280 to 320 nm) and a UV-A component (>320 nm) directly adjacent to the visible region of light. The effect on the human skin is particularly evident in the case of UV-B radiation in the form of sunburn. Accordingly, the industry offers a relatively large number of substances which adsorb UV-B radiation and thus prevent sunburn.

Dermatological investigations have shown that UV-A radiation is also entirely capable of causing skin damage and allergies, for example by damaging the keratin or elastin. This results in a reduction in elasticity and water storage capacity of the skin, i.e. the skin becomes less flexible and tends to wrinkle. The strikingly high frequency of skin cancer in regions of strong sunlight shows that damage to genetic information in the cells is apparently also caused by sunlight, especially by UV-A radiation. All this knowledge therefore makes the development of efficient filter substances for the UV-A and UV-B regions appear necessary.

In addition to known UV absorbers, for example 2-ethylhexyl 4-methoxycinnamate and 3-(4'-methyl) benzylidenebornan-2-one, light filters which, in the form of pigments, reflect or absorb UV rays are frequently also used in cosmetic and pharmaceutical formulations. The most important of these pigments are titanium dioxide and zinc oxide. At high concentrations, pigments can achieve full screening of the skin. However, the particles then reflect not only UV radiation, but also visible light, causing the frequently undesired strong inherent coloration of pigment-containing preparations.

Whereas titanium dioxide pigments with coarse particles (particle size >500 nm) have the comparable action in the UV-B and UV-A regions, the spectrum of action shifts toward the UV-B with decreasing particle size in the case of finely divided material. This shows that the absorption/reflection characteristics are directly dependent on the size and distribution of the particles. Balanced UV-B and UV-A protection therefore requires certain particle-size distributions.

It has been found to be disadvantageous on use of the abovementioned pigments that agglomeration, aggregation and/or separation of the pigment particles frequently occurs during storage of the cosmetic or pharmaceutical light filter formulations. The consequence of the modified optical properties can be a drastically reduced light protection action.

As an alternative to the abovementioned pigments, DE-A-196 19 460 describes the use of liquid-crystal mixtures having a cholesteric phase comprising a) liquid-crystalline organosiloxanes containing dianhydrohexatol derivatives as chiral groups, and b) chiral monomeric additives which induce the same helicity as the respective liquid-crystalline organosiloxanes, for the production of UV protection layers, in the form of films or flakes, which are suitable for cosmetic purposes. The liquid-crystal mixtures described here have the disadvantage that they can be converted into pigments only unsatisfactorily owing to their high viscosity.

DE-A-196 29 761 describes cosmetic or pharmaceutical preparations comprising polyorganosiloxane pigments having a viewing angle-dependent color. The pigments are at least one oriented, crosslinked substance of a liquid-crystalline structure with a chiral phase. Although the pigments disclosed here in the cosmetic and pharmaceutical formulations have certain absorption properties in the UV region, they have the disadvantage of certain applications of being colored compounds, whose range of applications is consequently restricted. However, there is very frequently a demand for precisely those cosmetic and pharmaceutical preparations by means of which UV protection is achieved, but in which coloration of the preparation is undesired.

It is an object of the present invention to provide novel light protection products for cosmetic and pharmaceutical purposes which act as filters in the UV-A and/or UV-B regions and which, in the form of pigments, do not have the abovementioned disadvantages.

We have found that this object is achieved by the use of cholesteric liquid-crystalline compositions comprising a) at least one chiral, liquid-crystalline, polymerizable monomer of the formula I, $$[Z^1\text{-}Y^1\text{-}(A^1)_m\text{-}Y^2\text{-}M^1\text{-}Y^3\text{-}]_n\text{-}X \qquad \text{I}$$

by means of which a cholesteric liquid-crystalline phase having a pitch of less than 450 nm can be obtained, where the variables, independently of one another, have the following meanings:

$A^1$ is a spacer having a chain length of from 1 to 30 carbon atoms, $Y^1$ to $Y^3$ are a chemical bond, —O—, —S—, —C(=O)—O—, —O—C(=O)—, —CH=CH—C(=O)—O—, —O—C(=O)—O—, —C(=O)—N(R)— or —(R)N—C(=O)—, —$CH_2$—O—, —O—$CH_2$—, —CH=N—, —N=CH— or —N=N—, $M^1$ is a mesogenic group, R is hydrogen or $C_1$–$C_4$-alkyl, $Z^1$ is hydrogen, $C_1$–$C_4$-alkyl, a polymerizable group or a radical carrying a polymerizable group, X is an n-valent chiral radical, m is 0 or 1, n is from 1 to 6, where the radicals $Z^1$, $Y^1$, $Y^2$, $Y^3$, $A^1$ and $M^1$ may be identical or different and at least one radical $Z^1$ is a polymerizable group or a radical containing a polymerizable group if n is greater than 1, or b) a mixture of $b_1$) at least one achiral, liquid-crystalline, polymerizable monomer of the formula II $$Z^2\text{-}Y^4\text{-}(A^2)_o\text{-}Y^5\text{-}M^2\text{-}Y^6\text{-}(A^3)_p\text{-}Y^7\text{-}Z^3 \qquad \text{II}$$

where the variables, independently of one another, have the following meanings:

$A^2$ and $A^3$ are a spacer having a chain length of from 1 to 30 carbon atoms, $M^2$ is a mesogenic group, $Y^4$ to $Y^7$ are a chemical bond, —O—, —S—, —C(=O)—O—, —O—C(=O)—, —CH=CH—C (=O)—O—, —O—C(=O)—O—, —C(=O)—N($R^1$)— or —($R^1$)N—C(=O)—, —$CH_2$—O—, —O—$CH_2$—, —CH=N—, —N=CH— or —N=N—, $R^1$ is hydrogen or $C_1$–$C_4$-alkyl, o and p are 0 or 1, $Z^2$ and $Z^3$ are hydrogen, $C_1$–$C_4$-alkyl, a polymerizable group or a radical carrying a polymerizable group, where at least one of the variables $Z^2$ and $Z^3$ is a polymerizable group or a radical carrying a polymerizable group, and $b_2$) at least one chiral additive by means of which a cholesteric liquid-crystalline phase having a pitch of less than 450 nm can be obtained, as UV filters in cosmetic and pharmaceutical preparations for protecting the human skin or human hair against sunlight, alone or together with compounds which absorb in the UV region and are known per se for cosmetic and pharmaceutical preparations.

Suitable spacers $A^1$ are all groups known for this purpose. The spacers generally contain from 1 to 30, preferably from 1 to 12, particularly preferably from 1 to 6 carbon atoms and consist of predominantly linear aliphatic groups. They may be interrupted in the chain, for example by non-adjacent oxygen or sulfur atoms or imino or alkylimino groups, for example methylimino groups. Suitable substituents for the spacer chain are also fluorine, chlorine, bromine, cyano, methyl and ethyl.

Examples of representative spacers are:

$—(CH_2)_q—$, $—(CH_2CH_2O)_rCH_2CH_2—$, $—CH_2CH_2SCH_2CH_2—$, $—CH_2CH_2NHCH_2CH_2—$,

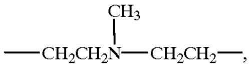, 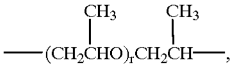,

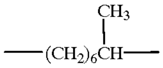 or 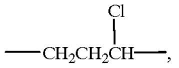, where r is from 1 to 3, and q is from 1 to 12.

Preferred spacers are ethylene, propylene, n-butylene, n-pentylene and n-hexylene.

However, it is also possible to link the mesogenic groups directly to the radical $Z^1$. In this case, m is 0 and $Y^1$ and $Y^2$ together are a chemical bond.

The radicals $M^1$ can be any known mesogenic groups, in particular mesogenic groups of the formula $(-T-Y^8)_s-T-$ where T are identical or different divalent, saturated or unsaturated iso- or heterocyclic radicals, $Y^8$ are groups as defined for $Y^1$ to $Y^7$, and s is 0, 1, 2 or 3, where, in the case where s>O, the radicals T and groups $Y^8$ may be identical or different amongst one another.

is preferably 1 or 2.

The radicals T may also be fluorine-, chlorine-, bromine-, cyano-, hydroxy- or nitro-substituted ring systems. Preferred radicals T are the following:

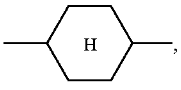, 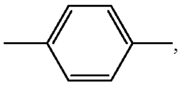,

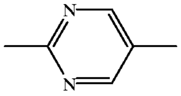 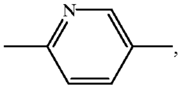,

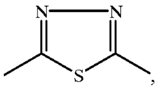, 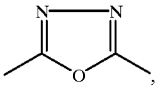,

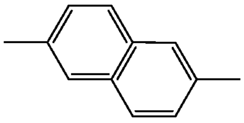, 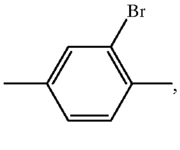,

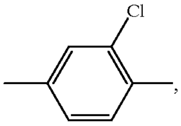, 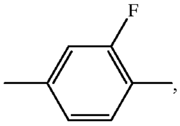,

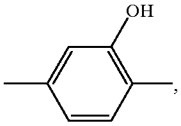, 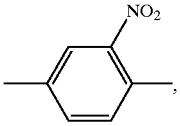,

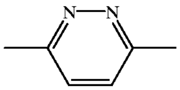 and 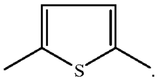.

Preferred mesogenic groups $M^1$ are, for example:

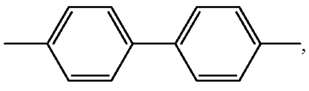,

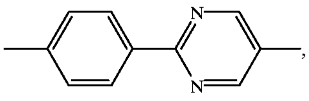,

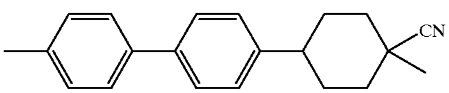,

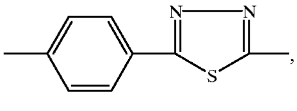,

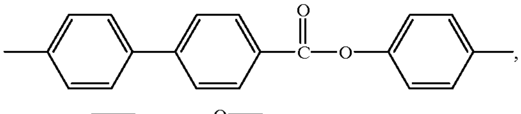,

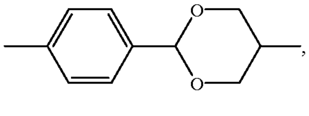,

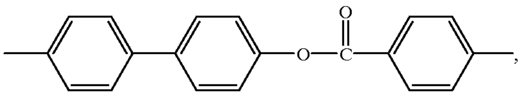,

-continued

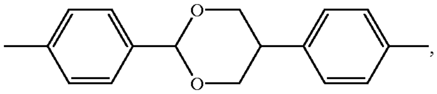

,

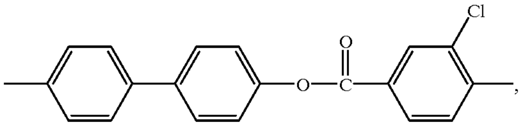

,

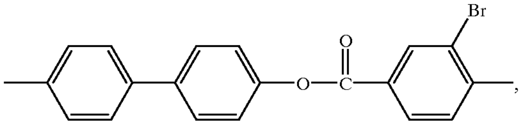

,

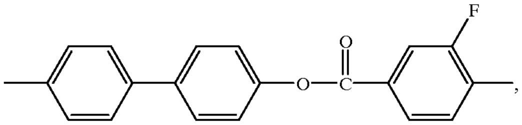

,

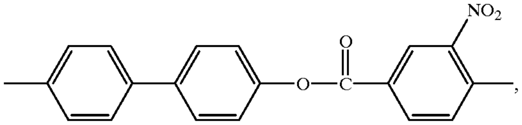

,

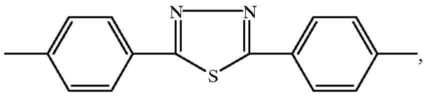

,

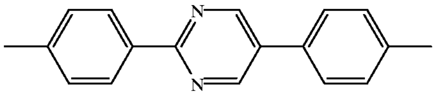

and

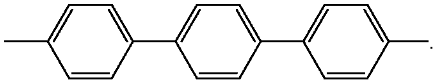

.

Particular preference is given to mesogenic groups $M^1$ of the following formulae:

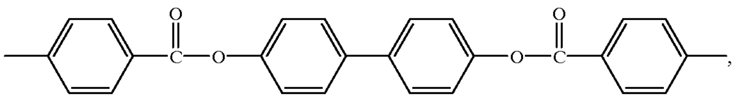

,

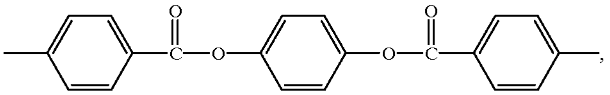

,

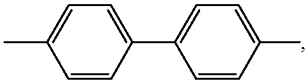

,

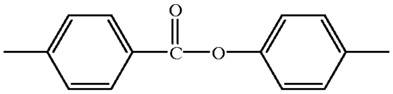

and

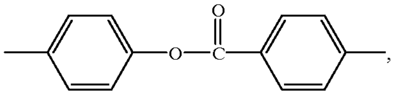

, where each aromatic ring can carry up to three identical or different substituents from the following group:

hydrogen, $C_1$–$C_{20}$-alkyl, $C_1$–$C_{20}$-alkoxy, $C_1$–$C_{20}$-alkoxycarbonyl, $C_1$–$C_{20}$-monoalkylaminocarbonyl, $C_1$–$C_{20}$-alkylcarbonyl, $C_1$–$C_{20}$-alkylcarbornyloxy, $C_1$–$C_{20}$-alkylcarbonylamino, formyl, halogen, cyano, hydroxyl or nitro.

Besides fluorine, chlorine, bromine, cyano, formyl and hydroxyl, preferred substituents for the aromatic rings are in particular short-chain aliphatic radicals, such as methyl, ethyl, n-propyl, i-propyl, n-butyl, i-butyl, sec-butyl, tert-butyl, and alkoxy, alkoxycarbonyl, alkylcarbonyl, alkylcarbonyloxy, alkylcarbonylamino and monoalkylaminocarbonyl radicals containing these alkyl groups.

The outer benzene rings in the particularly preferred groups $M^1$ preferably have the following substitution pattern:

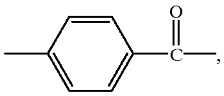

,

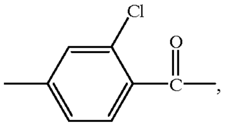

,

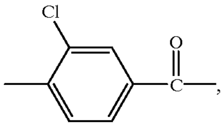

,

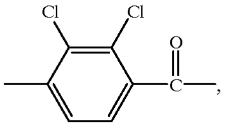

,

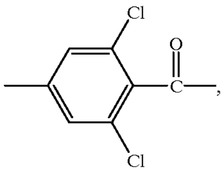

,

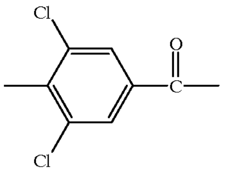

or

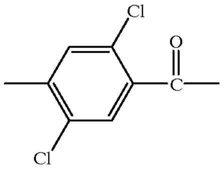

or are substituted analogously by F, Br, $CH_3$, $OCH_3$, CHO, $COCH_3$, $OCOCH_3$ or CN instead of Cl, it also being possible for the substituents to be mixed. Other structures which should be mentioned are

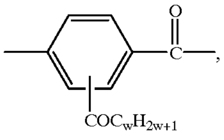

,

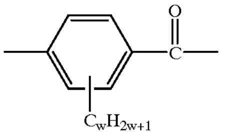

and

-continued
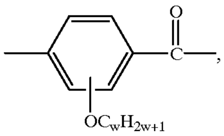
where w is from 2 to 20, preferably from 8 to 15.
The preferred substitution patterns of the central benzene ring of the particularly preferred groups $M^1$ are
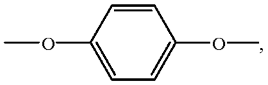
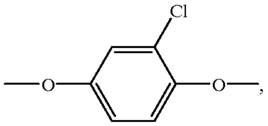
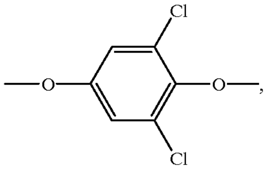
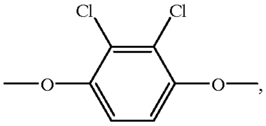
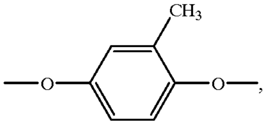
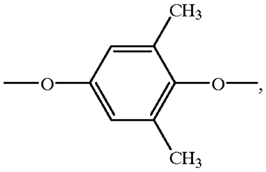
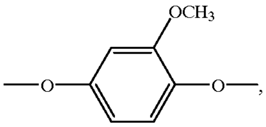
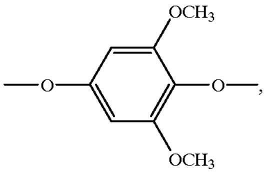
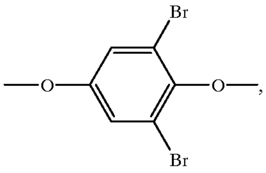
-continued
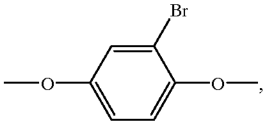
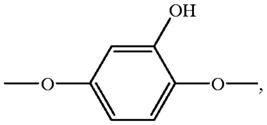
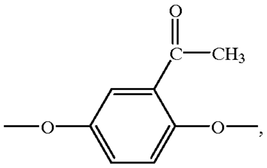
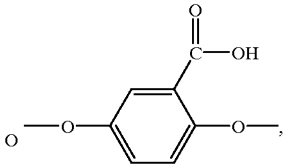
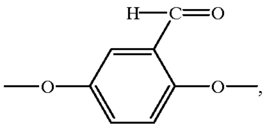
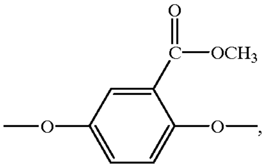
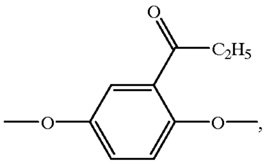
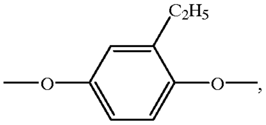
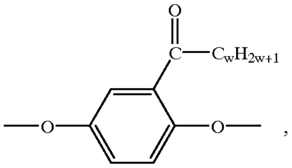
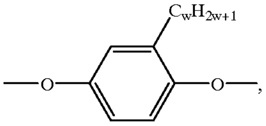
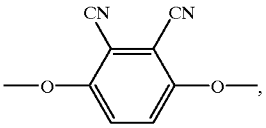

-continued

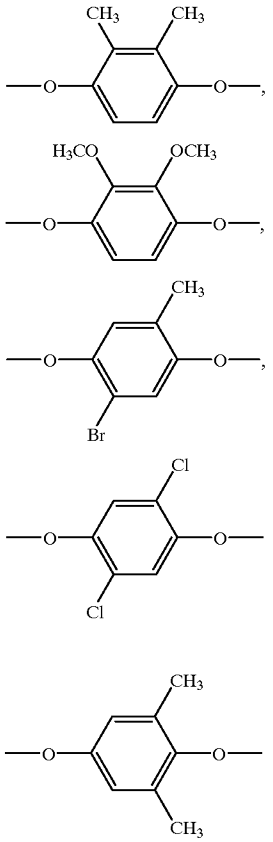

and

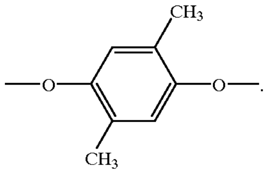

Preferred radicals $Z^1$ are:

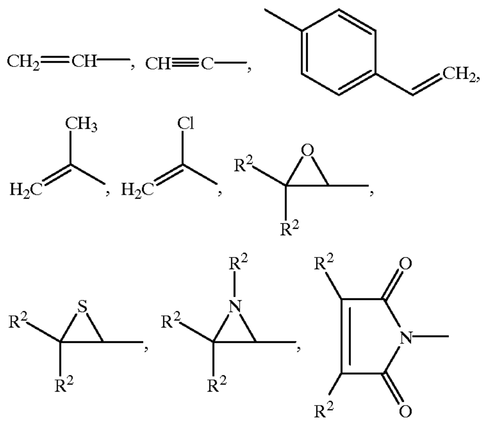

$—N{=}C{=}O$, $—N{=}C{=}S$, $—O—C{\equiv}N$, $—COOH$, $—OH$ and $NH_2$ where the radicals $R^2$ may be identical or different and are hydrogen or $C_1$–$C_4$-alkyl, such as methyl, ethyl, n-propyl, isopropyl, n-butyl, isobutyl, sec-butyl or tert-butyl. Of the reactive polymerizable groups, the cyanates can spontaneously trimerize to give cyanurates and are therefore preferred. For polymerization, the other groups mentioned require further compounds containing complementary reactive groups. Thus, for example, isocyanates can be polymerized with alcohols to give urethanes and with amines to give urea derivatives. A similar situation applies to thiiranes and aziridines. Carboxyl groups can be condensed to form polyesters and polyamides. The maleimido group is particularly suitable for free-radical copolymerization with olefinic compounds, such as styrene. The complementary reactive groups here may either be present in the second compound according to the invention, which is mixed with the first, or can be incorporated into the polymeric network via auxiliary compounds containing 2 or more of these complementary groups.

Particularly preferred groups $Z^1$-$Y^1$ are acrylate and methacrylate.

$Y^1$–$Y^3$ can be as defined above, with the term chemical bond being taken to mean a single covalent bond.

Suitable alkyl radicals R and $Z^1$ are branched and unbranched $C_1$–$C_4$-alkyl chains, preferably methyl, ethyl, n-propyl, 1-methylethyl, n-butyl, 1-methylpropyl, 2-methylpropyl and 1,1-dimethylethyl.

Of the chiral radicals X in the compounds of formula I, particular preference is given, inter alia owing to their availability, to those derived from sugars, binaphthyl or biphenyl derivatives and from optically active glycols, dialcohols or amino acids. In the case of sugars, particular mention should be made of pentoses and hexoses and derivatives thereof.

Examples of radicals X are the following structures, where the terminal dashes in each case indicate the free valences:

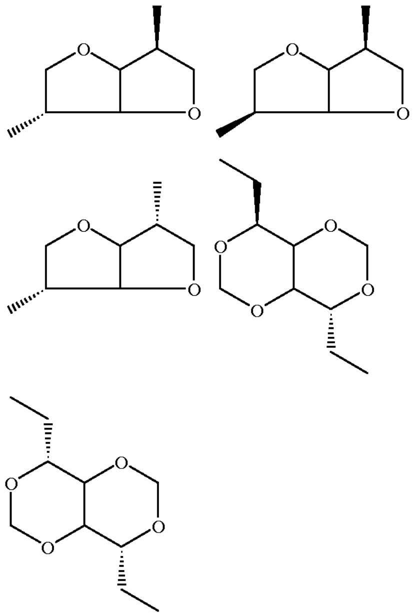

-continued
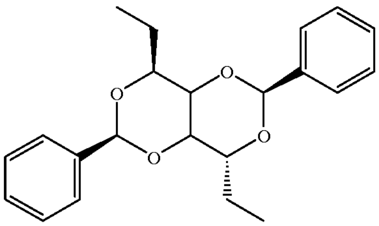
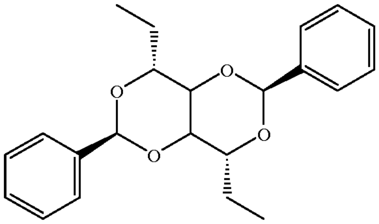
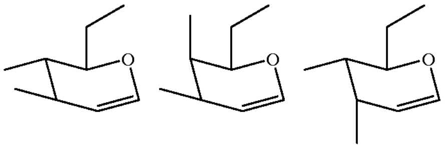
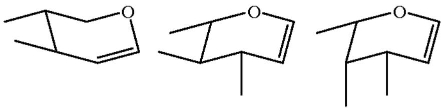
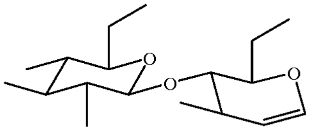
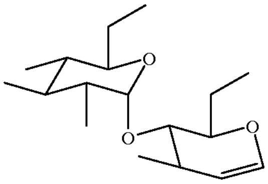
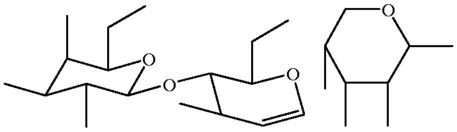
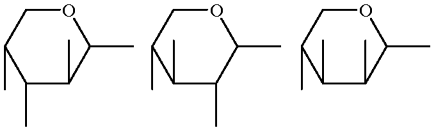
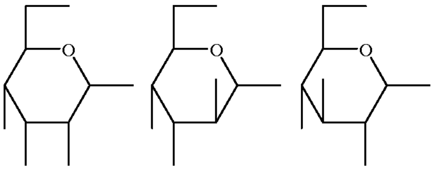
-continued
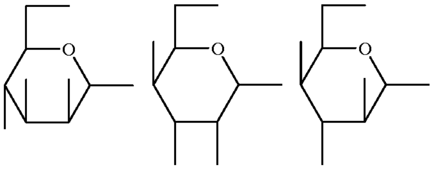
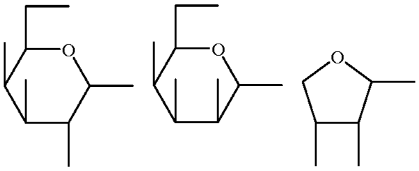
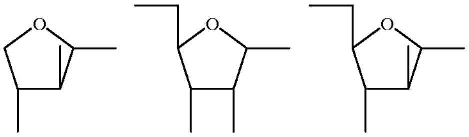
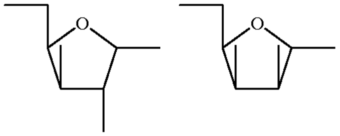
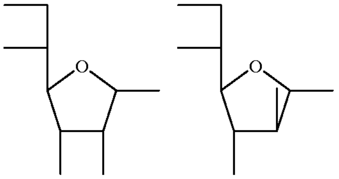
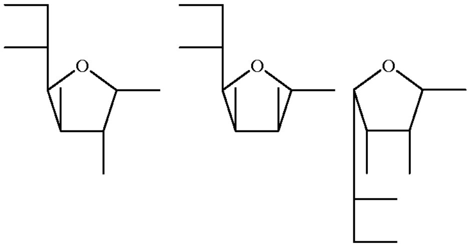
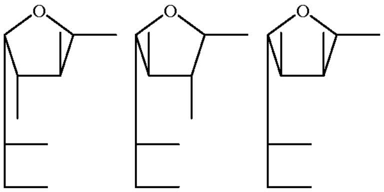
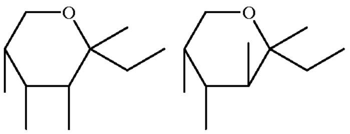
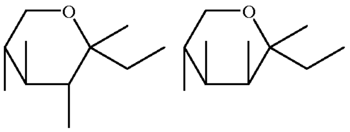

-continued

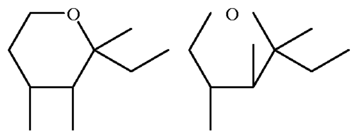

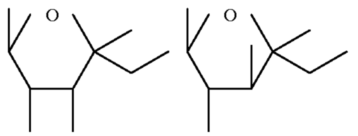

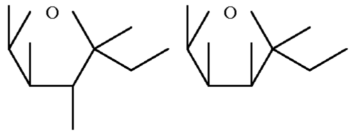

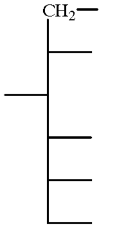

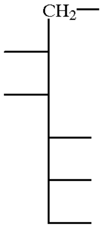

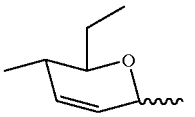

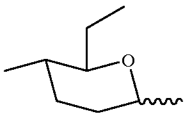

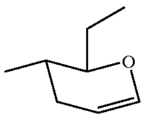

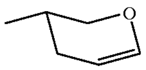

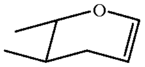

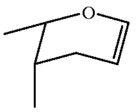

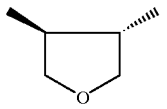

Particular preference is given to the following:

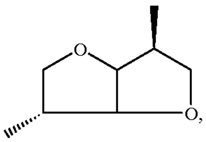

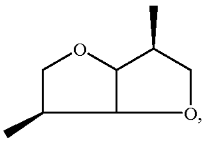

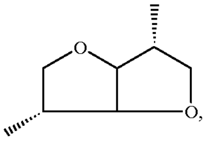

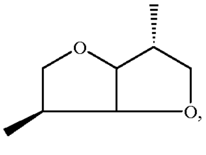

and

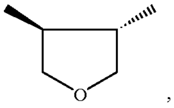

,

Also suitable are chiral groups containing the following structures:

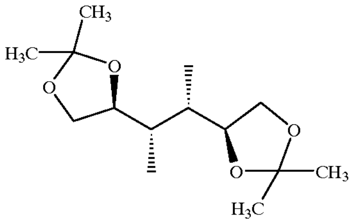

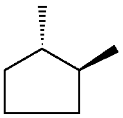

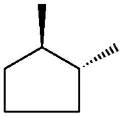

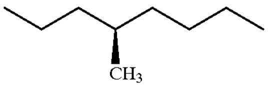

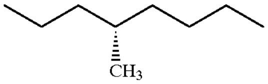

Further examples are given in German Application P 43 42 280.2.

m is preferably 1, and n is preferably 2.

Component $b_1$) in the polymerizable mixture b) for the use according to the invention is at least one achiral, liquid-crystalline polymerizable monomer of the formula II $$Z^2\text{-}Y^4\text{-}(A^2)_o\text{-}Y^5\text{-}M^2\text{-}Y^6\text{-}(A^3)_p\text{-}Y^7\text{-}Z^3 \qquad \text{II}$$

where the variables, independently of one another, have the following meanings:

$A^2$ and $A^3$ are a spacer having a chain length of from 1 to 30 carbon atoms, $M^2$ is a mesogenic group, $Y^4$ to $Y^7$ are a chemical bond, —O—, —S—, —C(=O)—O—, —O—C(=O)—, —CH=CH—C(=O)—O—, —O—C(=O)—O—, —C(=O)—N($R^1$)— or —($R^1$)N—C(=O)—, —$CH_2$—O—, —O—$CH_2$—, —CH=N—, —N=CH— or —N=N—, $R^1$ is hydrogen or $C_1$–$C_4$-alkyl, o and p are 0 or 1

$Z^2$ and $Z^3$ are hydrogen, $C_1$–$C_4$-alkyl, a polymerizable group or a radical carrying a polymerizable group, where at least one of the variables $Z^2$ and $Z^3$ is a polymerizable group or a radical carrying a polymerizable group.

The same preferences as for the corresponding variables of the formula I apply here to the polymerizable groups, the bridges $Y^4$ to $Y^7$, the spacers and the mesogenic group.

As in the formula I, it is also possible to link the mesogenic group directly to the radicals $Z^2$ or $Z^3$. In these cases, o and/or p are 0, and $Y^4$ and $Y^5$ and/or $Y^6$ and $Y^7$ together are a chemical bond.

In addition, the mixture b) also contains a chiral additive $b_2$).

Known chiral dopants for liquid-crystalline phases are numerous compounds (for example disclosed in DE-A 43 42 280 and DE-A 196 11 101). Suitable dopants should have a high twisting power in order that small amounts of the dopant are sufficient to induce the helical structure. In addition, the chiral dopants should exhibit good compatibility with the liquid-crystalline compounds, enabling effective interaction between these components.

The extent of the twisting in each case depends on the twisting power of the chiral dopant and on its concentration. The pitch of the helix and in turn the interference wavelength is thus dependent on the concentration of the chiral dopant. It is therefore not possible to give a generally valid concentration range for the dopant. The dopant is added in the amount which achieves the desired UV reflection.

Preferred chiral additives for $b_2$) are compounds of the formula III $$[Z^1\text{-}Y^1\text{-}(A^1)_m\text{-}Y^2\text{-}M^3\text{-}Y^3\text{-}]_n\text{-}X \qquad \text{III}$$

where $Z^1$, $Y^1$, $Y^2$, $Y^3$, $A^1$, X, m and n are as defined above, and $M^3$ is a divalent radical containing at least one heterocyclic or isocyclic ring system.

The moiety of $M^3$ is similar to the mesogenic groups described above since particularly good compatibility with she liquid-crystalline compound is achieved in this way. However, $M^3$ need not be mesogenic, since the compound III should cause a corresponding twisting of the liquid-crystalline phase merely through its chiral structure. Preferred ring systems present in $M^3$ are the abovementioned structures T; preferred structures $M^3$ are those of the abovementioned formula $(T\text{-}Y^8)_s\text{-}T$. Further monomers and chiral compounds from group b) are described in WO 97/00600 and its parent DE-A-195 324 08, which is expressly incorporated herein in full by way of reference.

The cholesteric, liquid-crystalline compositions preferably used as UV filters in cosmetic and pharmaceutical preparations comprise a mixture of at least one achiral, liquid-crystalline, polymerizable monomer of the formula II and at least one chiral, polymerizable monomer of the formula III.

Particularly preferred monomers II which may be mentioned are the following structures:

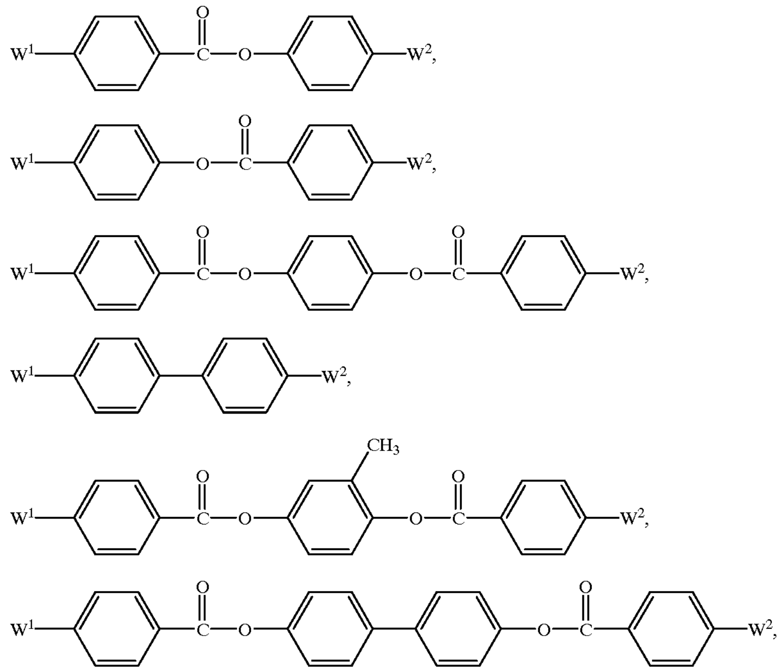

$W^1$: $CH_2{=}CH{-}C({=}O){-}O{-}(CH_2)_4{-}O{-}$, $W^2$: ${-}O{-}(CH_2)_4{-}O{-}C({=}O){-}CH{=}CH_2$

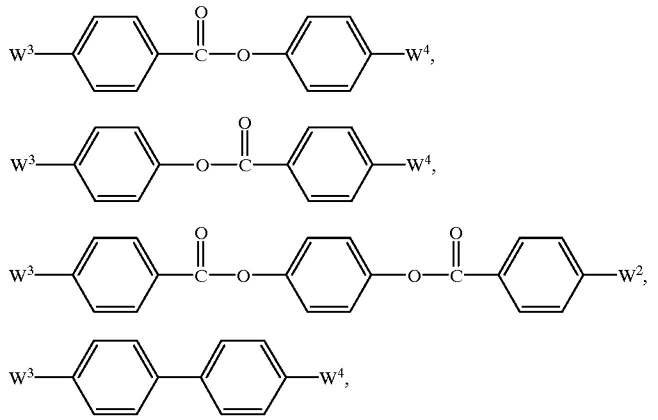

-continued
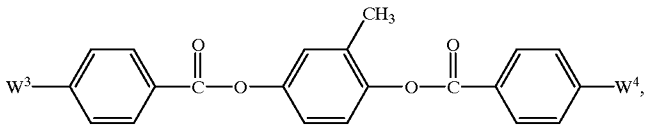
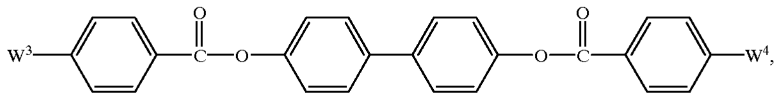
$W^3$: $CH_2{=}CH{-}C({=}O){-}O{-}(CH_2)_6{-}O{-}$, $W^4$: ${-}O{-}(CH_2)_6{-}O{-}C({=}O){-}CH{=}CH_2$
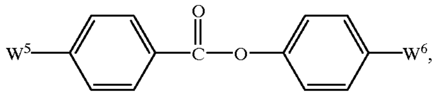
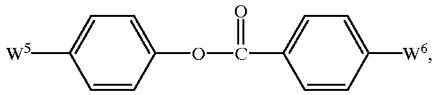
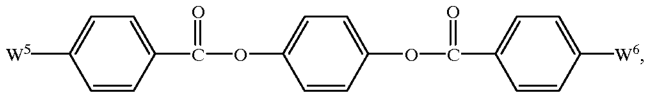
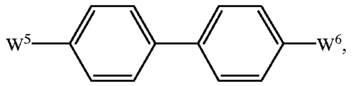
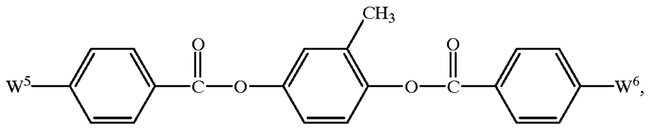
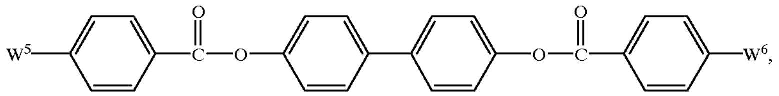
$W^5$: $CH_2{=}C(CH_3){-}C({=}O){-}O{-}(CH_2)_4{-}O{-}$, $W^6$: ${-}O{-}(CH_2)_4{-}O{-}C({=}O){-}C(CH_3){=}CH_2$
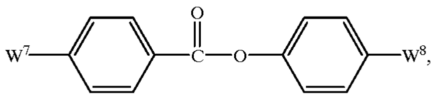
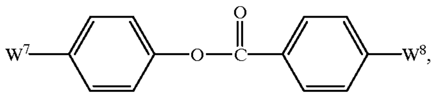
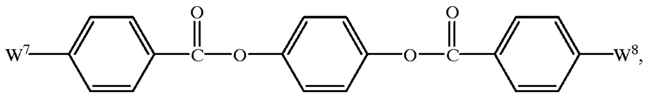
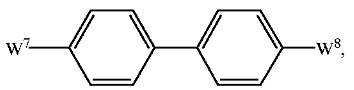
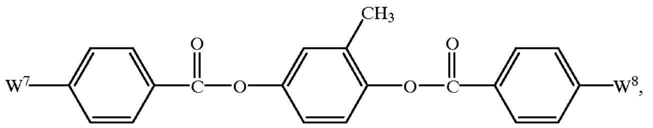
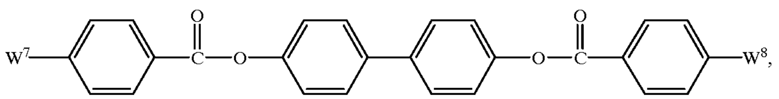
$W^7$: $CH_2{=}C(CH_3){-}C({=}O){-}O{-}(CH_2)_6{-}O{-}$, $W^8$: ${-}O{-}(CH_2)_6{-}O{-}C({=}O){-}C(CH_3){=}CH_2$ -continued
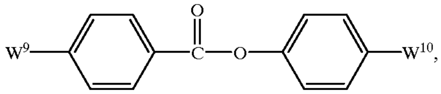,
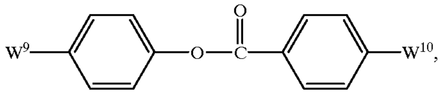,
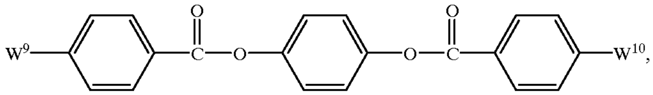,
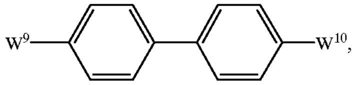,
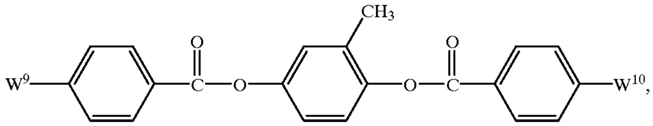,
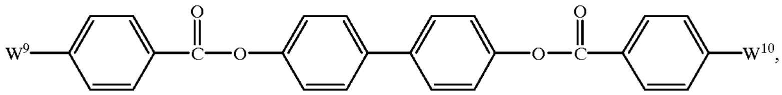,
$W^9$: $CH_2{=}CH{-}C({=}O){-}O{-}(CH_2)_4{-}O{-}C({=}O){-}O{-}$,
$W^{10}$: ${-}O{-}(O{=})C{-}O{-}(CH_2)_4{-}O{-}C({=}O){-}CH{=}CH_2$
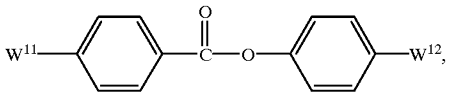,
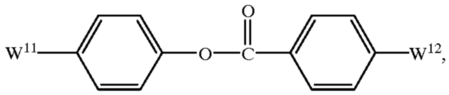,
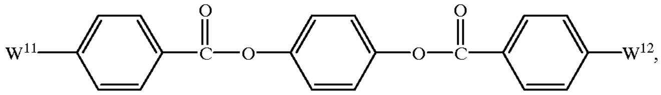,
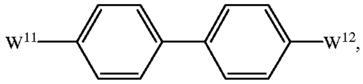,
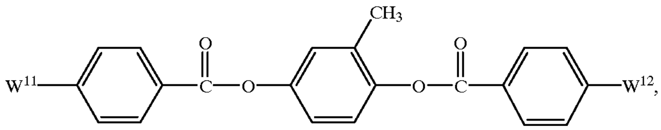,
$W^{11}$: $CH_2{=}CH{-}C({=}O){-}O{-}(CH_2)_6{-}O{-}C({=}O){-}O{-}$,
$W^{12}$: ${-}O{-}(O{=})C{-}O{-}(CH_2)_6{-}O{-}C({=}O){-}CH{=}CH_2$
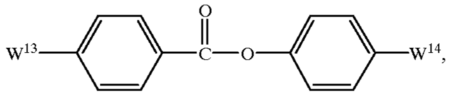,
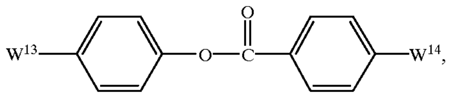,
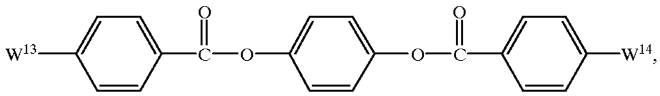, -continued
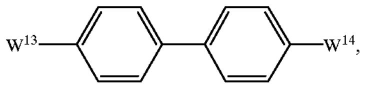
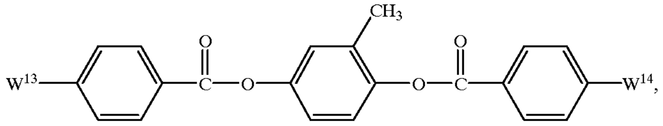
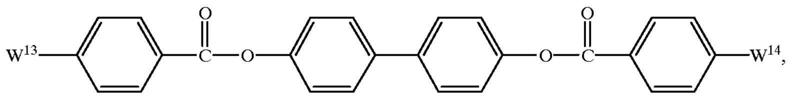
$W^{13}$: $CH_2{=}C(CH_3){-}C({=}O){-}O{-}(CH_2)_4{-}O{-}C({=}O){-}O{-}$,
$W^{14}$: ${-}O{-}(O{=})C{-}O{-}(CH_2)_4{-}O{-}C({=}O){-}C(CH_3){=}CH_2$
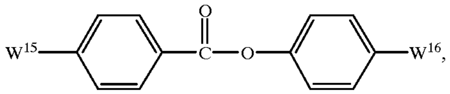
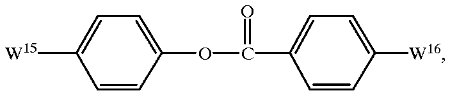
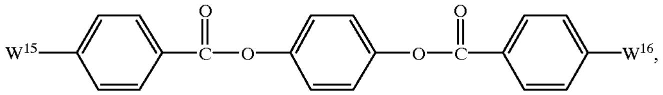
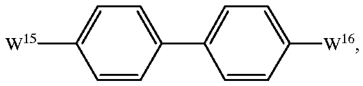
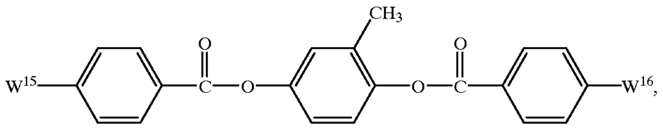
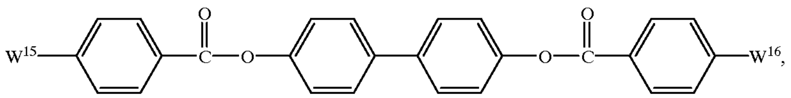
$W^{15}$: $CH_2{=}C(CH_3){-}C({=}O){-}O{-}(CH_2)_6{-}O{-}C({=}O){-}O{-}$,
$W^{16}$: ${-}O{-}(O{=})C{-}O{-}(CH_2)_6{-}O{-}C({=}O){-}C(CH_3){=}CH_2$.
Particularly preferred monomers III which may be mentioned are the following structures:
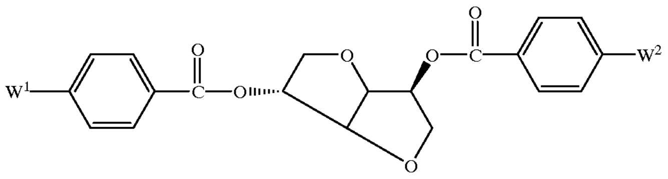
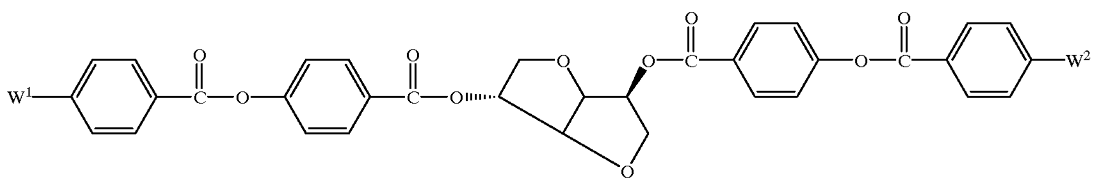
$W^1$: $CH_2{=}CH{-}C({=}O){-}O{-}(CH_2)_4{-}O{-}$ $W^2$: ${-}O{-}(CH_2)_4{-}O{-}C({=}O){-}CH{=}CH_2$ -continued
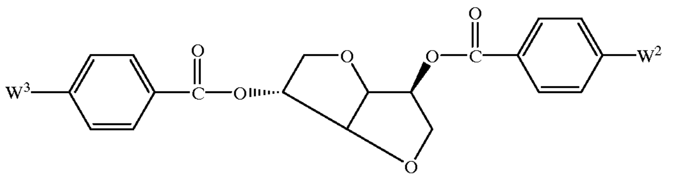
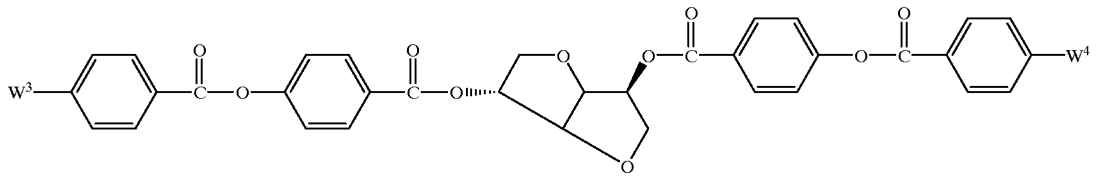
$W^3$: $CH_2{=}CH{-}C({=}O){-}O{-}(CH_2)_6{-}O{-}$ $W^4$: ${-}O{-}(CH_2)_6{-}O{-}C({=}O){-}CH{=}CH_2$
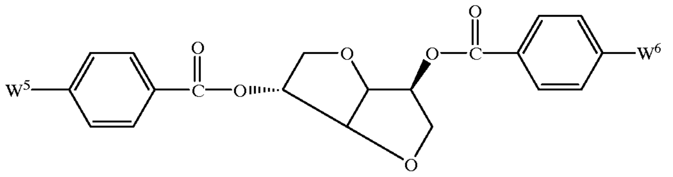
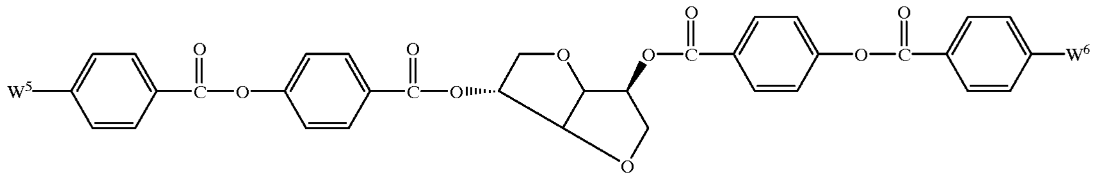
$W^5$: $CH_2{=}C(CH_3){-}C({=}O){-}O{-}(CH_2)_4{-}O{-}$, $W^6$: ${-}O{-}(CH_2)_4{-}O{-}C({=}O){-}C(CH_3){=}CH_2$
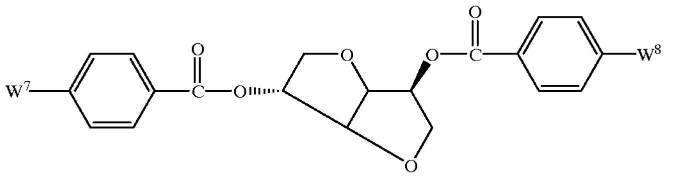
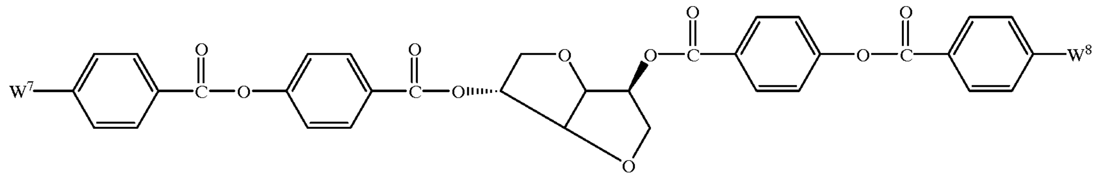
$W^7$: $CH_2{=}C(CH_3){-}C({=}O){-}O{-}(CH_2)_6{-}O{-}$, $W^8$: ${-}O{-}(CH_2)_6{-}O{-}C({=}O){-}C(CH_3){=}CH_2$
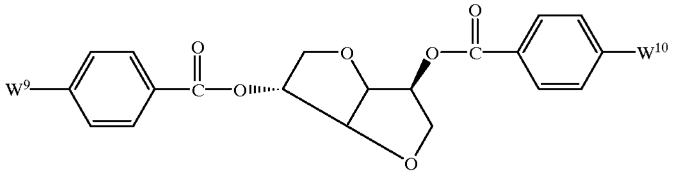
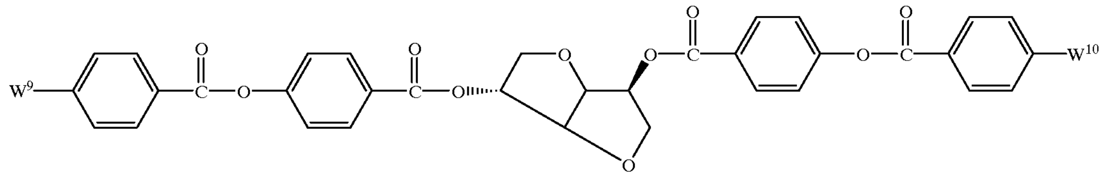
$W^9$: $CH_2{=}CH{-}C({=}O){-}O{-}(CH_2)_4{-}O{-}C({=}O){-}O{-}$ $W^{10}$: ${-}O{-}(O{=})C{-}O{-}(CH_2)_4{-}O{-}C({=}O){-}CH{=}CH_2$ -continued
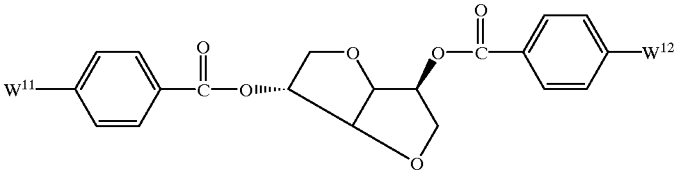
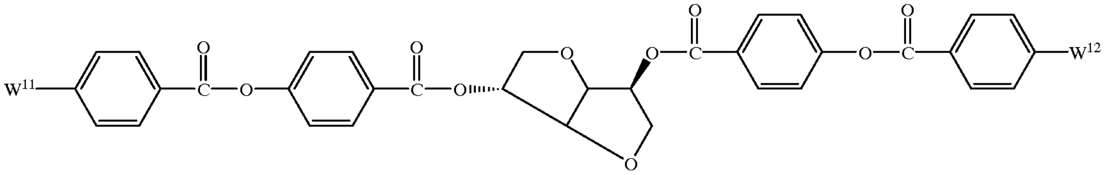
$W^{11}$: $CH_2{=}CH{-}C({=}O){-}O{-}(CH_2)_6{-}O{-}C({=}O){-}O{-}$
$W^{12}$: ${-}O{-}(O{=})C{-}O{-}(CH_2)_6{-}O{-}C({=}O){-}CH{=}CH_2$
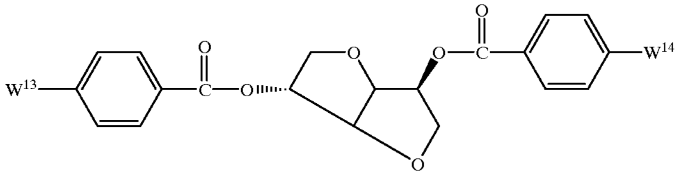
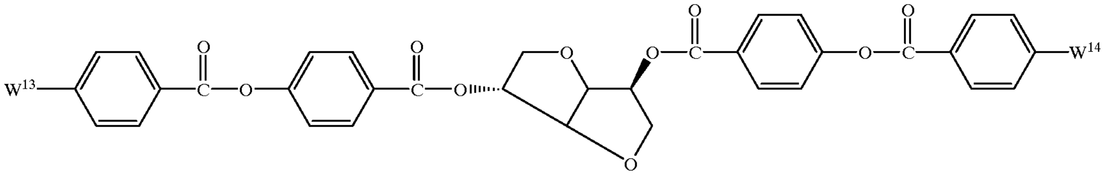
$W^{13}$: $CH_2{=}C(CH_3){-}C({=}O){-}O{-}(CH_2)_4{-}O{-}C({=}O){-}O{-}$,
$W^{14}$: ${-}O{-}(O{=})C{-}O{-}(CH_2)_4{-}O{-}C({=}O){-}C(CH_3){=}CH_2$
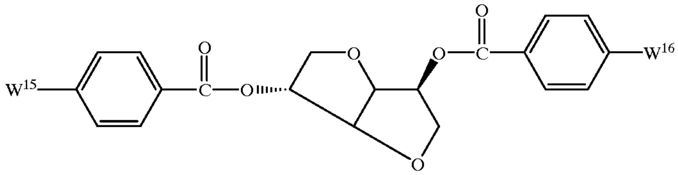
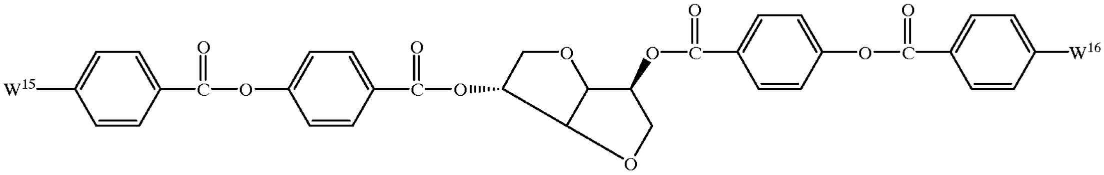
$W^{15}$: $CH_2{=}C(CH_3){-}C({=}O){-}O{-}(CH_2)_6{-}O{-}C({=}O){-}O{-}$,
$W^{16}$: ${-}O{-}(O{=})C{-}O{-}(CH_2)_6{-}O{-}C({=}O){-}C(CH_3){=}CH_2$
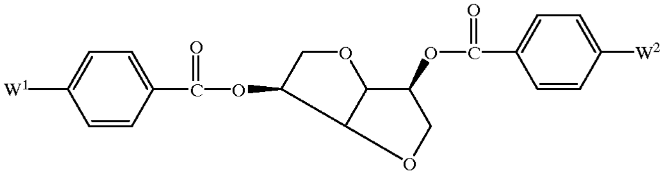
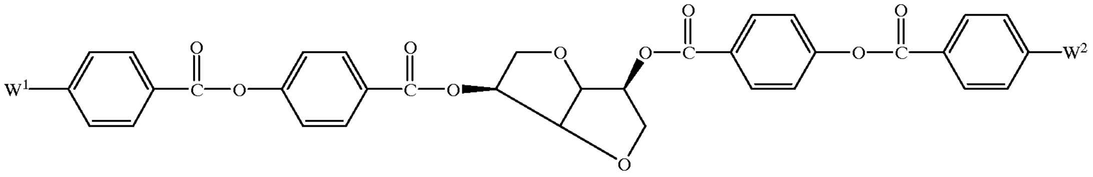
$W^1$: $CH_2{=}CH{-}C({=}O){-}O{-}(CH_2)_4{-}O{-}$
$W^2$: ${-}O{-}(CH_2)_4{-}O{-}C({=}O){-}CH{=}CH_2$ -continued
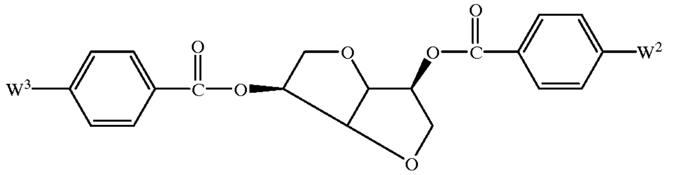
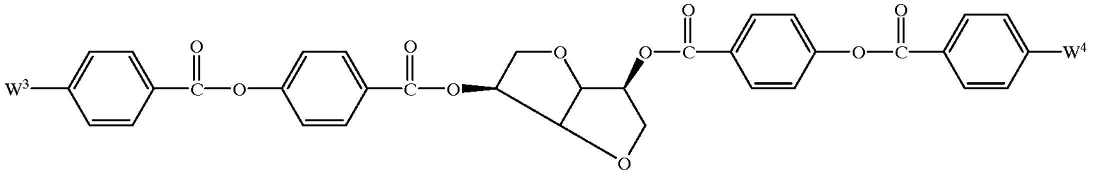
$W^3$: $CH_2{=}CH{-}C({=}O){-}O{-}(CH_2)_6{-}O{-}$ $W^4$: ${-}O{-}(CH_2)_6{-}O{-}C({=}O){-}CH{=}CH_2$
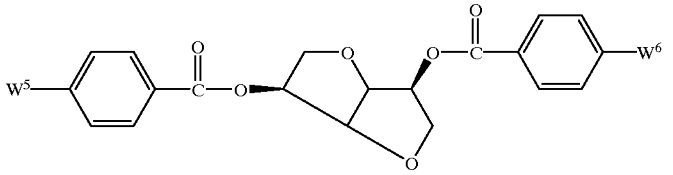
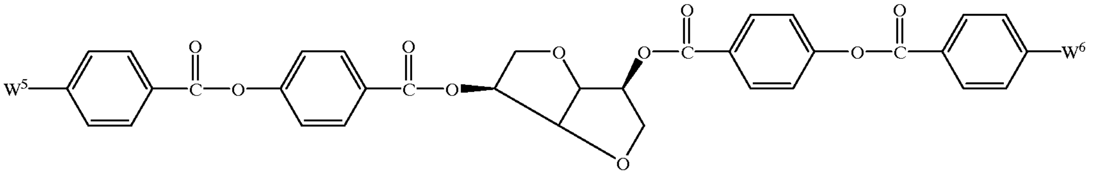
$W^5$: $CH_2{=}C(CH_3){-}C({=}O){-}O{-}(CH_2)_4{-}O{-}$, $W^6$: ${-}O{-}(CH_2)_4{-}O{-}C({=}O){-}C(CH_3){=}CH_2$
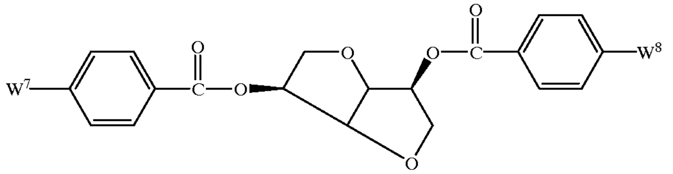
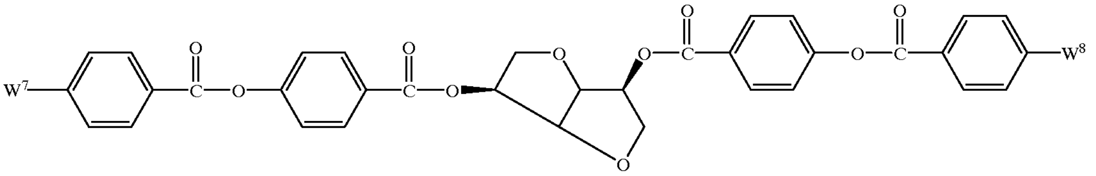
$W^7$: $CH_2{=}C(CH_3){-}C({=}O){-}O{-}(CH_2)_6{-}O{-}$, $W^8$: ${-}O{-}(CH_2)_6{-}O{-}C({=}O){-}C(CH_3){=}CH_2$
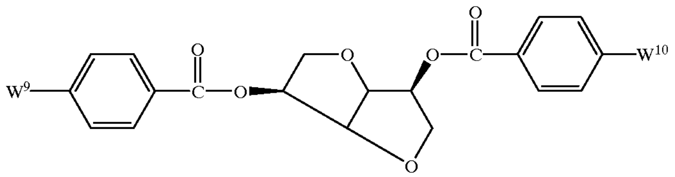
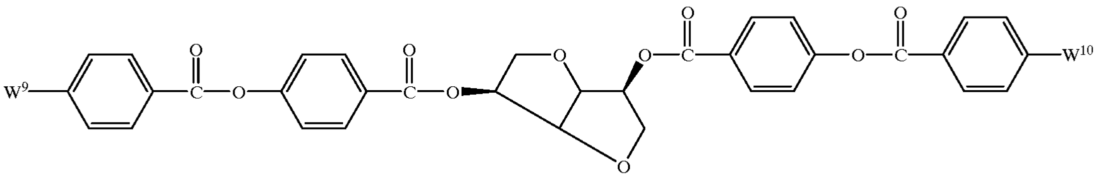
$W^9$: $CH_2{=}CH{-}C({=}O){-}O{-}(CH_2)_4{-}O{-}C({=}O){-}O{-}$
$W^{10}$: ${-}O{-}(O{=})C{-}O{-}(CH_2)_4{-}O{-}C({=}O){-}CH{=}CH_2$ -continued

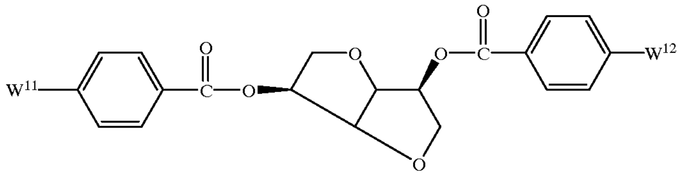

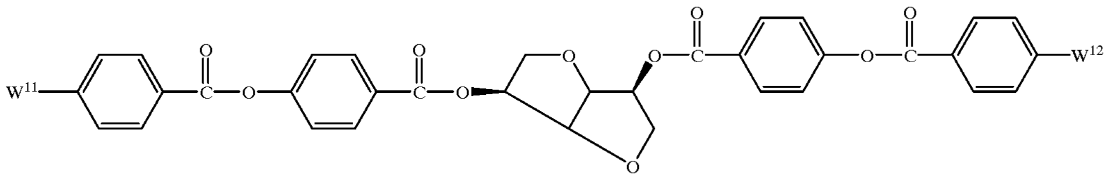

$W^{11}$: $CH_2{=}CH{-}C({=}O){-}O{-}(CH_2)_6{-}O{-}C({=}O){-}O{-}$ $W^{12}$: $-O{-}(O{=})C{-}O{-}(CH_2)_6{-}O{-}C({=}O){-}CH{=}CH_2$

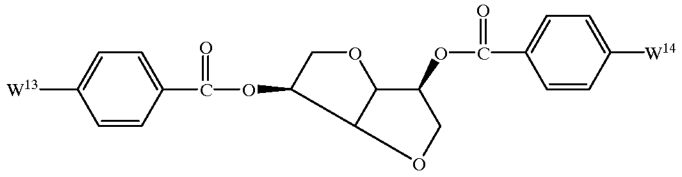

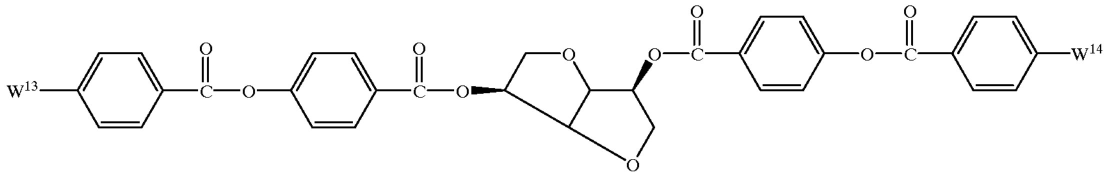

$W^{13}$: $CH_2{=}C(CH_3){-}C({=}O){-}O{-}(CH_2)_4{-}O{-}C({=}O){-}O{-}$, $W^{14}$: $-O{-}(O{=})C{-}O{-}(CH_2)_4{-}O{-}C({=}O){-}C(CH_3){=}CH_2$

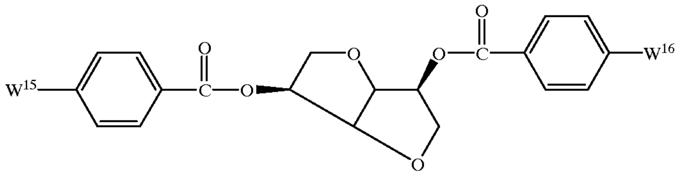

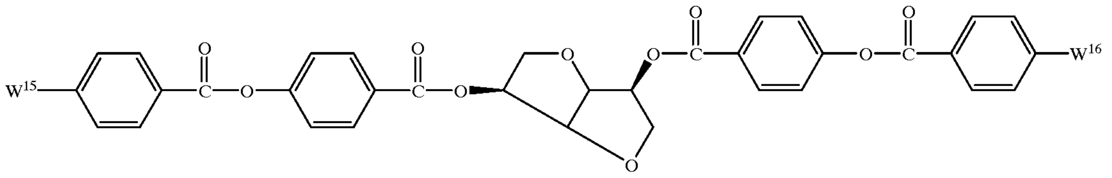

$W^{15}$: $CH_2{=}C(CH_3){-}C({=}O){-}O{-}(CH_2)_6{-}O{-}C({=}O){-}O{-}$, $W^{16}$: $-O{-}(O{=})C{-}O{-}(CH_2)_6{-}O{-}C({=}O){-}C(CH_3){=}CH_2$.

The weight ratios between component II and component III are in the range from 99:1 to 40:60, preferably in the range from 99:1 to 70:30, particularly preferably in the range from 98:2 to 85:15.

The abovementioned compounds are prepared in a manner known per se as described in DE-A-195 32 408, DE-A-44 08 171, EP-A-0 750 029 and WO 95/16007. For further details, reference is made to these publications.

For the novel use of the abovementioned cholesteric, liquid-crystalline compositions a) and b) as UV filters in cosmetic and pharmaceutical preparations, the components of the formulae I to III present in these compositions can be incorporated directly into the cosmetic and pharmaceutical preparations.

Preferably, however, the cholesteric, liquid-crystalline compositions used in accordance with the invention are employed in the form of pigments. These pigments are obtainable by converting the monomers I to III present in the cholesteric, liquid-crystalline compositions into highly crosslinked polymers having a frozen liquid-crystalline order structure with the aid of their polymerizable groups by free-radical or ionic polymerization processes, which can be initiated by a photochemical reaction.

The preparation of these pigments is known and is described in detail in German Application P 19738369.6.

In addition, an overview of processes for the photochemical crosslinking of oriented starting materials is given in C. G. Roffey, Photopolymerization of Surface Coatings, (1982) John Willey & Sons, Chichester, pp. 137 to 208.

In a preferred embodiment, the three-dimensionally crosslinkable, polymerizable monomers are applied to a substrate, crosslinked on this substrate and detached from the substrate after the crosslinking.

The cholesteric, liquid-crystalline compositions which have been crosslinked to give a film can, after the polymerization, be comminuted to the particle size desired in each case by grinding. Depending on the desired application and the type of cosmetic or pharmaceutical formulation, particles having a diameter of from 1 to 1000 $\mu$m can be produced. Preferred particle sizes are in the range from 1 to 100 $\mu$m, particularly preferably in the range from to 50 $\mu$m.

The thickness of the pigments is from 1 to 100 $\mu$m, preferably from 1 to 50 $\mu$m, particularly preferably from 1.5 to 10 $\mu$m.

The cholesteric, liquid-crystalline compositions a) and b) which are suitable as starting substances for the preparation of the pigments have a twisted structure with a pitch corresponding to a light wavelength of up to 450 nm. As shown in the preferred embodiments b), these twisted structures having a defined pitch can be obtained from nematic structures $b_1$) by adding a chiral substance $b_2$). The nature and proportion of the chiral substance determine the pitch of the twisted structure and thus the wavelength of the reflected light. Depending on the chirality of the optically active additives employed, the twist of the structure can be either left-handed or right-handed.

So-called broad-band reflectors can be produced by simply mixing a plurality of the cholesteric, liquid-crystalline pigments to be used in accordance with the invention, each with different UV reflection maxima.

In addition, it is possible to achieve complete reflection of the UV rays by mixing at least two different pigments in the cholesteric, liquid-crystalline compositions a) and/or b) with opposite twist (helicity). Pigments having such cholesteric, liquid-crystalline structures of opposite twist are obtainable, for example, by adding the individual mirror-image isomers (enantiomers) or diastereomers of the chiral additives $b_2$) to the achiral, liquid-crystalline, polymerizable monomer $b_1$). The pitch of the structures of opposite twist can be identical or different.

It is also possible firstly to mix the cholesteric, liquid-crystalline compositions a) or b) of opposite twist and then to convert the mixture into the above-described pigments by the abovementioned crosslinking and to employ the pigments as UV reflectors in cosmetic and pharmaceutical formulations.

Besides the abovementioned mixtures of cholesteric, liquid-crystalline pigments, it is also possible to prepare multilayer pigments whose individual layers comprise different three-dimensionally crosslinked, cholesteric, liquid-crystalline compositions to be used in accordance with the invention. The design of such multilayer pigments can be varied widely. Thus, inter alia,

- individual layers of crosslinked cholesteric, liquid-crystalline compositions of opposite twist or
- individual layers of crosslinked, cholesteric, liquid-crystalline compositions having the same twist direction, but different pitch and thus different reflection properties, can be applied one on top of the other.

Preference is given to so-called three-layer pigments, in which the two outer layers each consist of one of the crosslinked, cholesteric, liquid-crystalline compositions to be used in accordance with the invention, and the middle layer can comprise, for example, a binder matrix, in which, in addition, a further UV absorber may be embedded. Details on the preparation, properties and further constituents of such multilayer, cholesteric pigments are given in German Patent Application P 19738368.8.

The invention thus also relates to the above-described pigments, in particular multilayer pigments, comprising the cholesteric, liquid-crystalline compositions mentioned at the outset.

An advantage of the pigments to be used in accordance with the invention is that their composition can be customized so that the desired UV reflection can be achieved using these pigments without exhibiting any inherent color (in the visible region).

A further advantage of the pigments consists in their physical properties. Owing to their low density (compared, for example, with $TiO_2$), the pigments can readily be incorporated into emulsions without any aggregation or separation of pigment particles.

The pigments to be used in accordance with the invention can be incorporated into the cosmetic and pharmaceutical preparations by simple mixing.

The present invention furthermore relates to cosmetic and pharmaceutical preparations comprising from 0.1 to 20% by weight, preferably from 0.5 to 10% by weight, particularly preferably from 1 to 7% by weight, based on the total amount of the cosmetic and pharmaceutical preparation, of one or more of the cholesteric, liquid-crystalline compositions comprising a) at least one chiral, liquid-crystalline, polymerizable monomer of the formula I $[(Z^1\text{-}Y^1\text{-}(A^1)_m\text{-}Y^2\text{-}M^1\text{-}Y^3\text{-})_n\text{-}X]$, by means of which a cholesteric, liquid-crystalline phase with a pitch of less than 450 nm can be achieved, or b) a mixture of at least one achiral, liquid-crystalline, polymerizable monomer of the formula II $(Z^2\text{-}Y^4\text{-}(A^2)_o\text{-}Y^5\text{-}M^2\text{-}Y^6\text{-}(A^3)_p\text{-}Y^7\text{-}Z^3)$ and at least one chiral additive, by means of which a cholesteric, liquid-crystalline phase with a pitch of less than 450 nm can be achieved, together with compounds which absorb in the UV-A and UV-B region which are known per se for cosmetic and pharmaceutical preparations, as light protection agents. The variables in the formulae I and II and the class of the chiral additives employed correspond in both their general and preferred embodiments, to the explanations already outlined above.

Preference is given to those of the abovementioned cosmetic and pharmaceutical preparations which comprise the cholesteric, liquid-crystalline compositions to be used in accordance with the invention in the form of the pigments described above, in particular in the form of multilayer pigments.

The cosmetic and pharmaceutical preparations containing light protection agents are generally based on a carrier comprising at least one oil phase. However, preparations based exclusively on water are also possible if compounds having hydrophilic substituents are used. Accordingly, oils, oil-in-water and water-in-oil emulsions, creams and pastes, compositions for lip protection sticks and fat-free gels are suitable.

Sun protection preparations of this type can accordingly, be in liquid, pasty or solid form, for example as water-in-oil creams, oil-in-water creams and lotions, aerosol foam creams, gels, oils, fat sticks, powders, sprays or alcoholic/aqueous lotions.

Conventional oil components in cosmetics are, for example, paraffin oil, glyceryl stearate, isopropyl myristate, diisopropyl adipate, stearyl 2-ethylhexanoate, hydrogenated polyisobutene, vaseline, caprylic acid/caproic acid triglycerides, microcrystalline wax, lanolin and stearic acid.

Conventional cosmetic auxiliaries which are suitable as additives are, for example, coemulsifiers, fats and waxes, stabilizers, thickeners, biogenic active ingredients, film formers, fragrances, colorants, pearlescent agents, preservatives, pigments, electrolytes (for example magnesium sulfate) and pH regulators. Preferred coemulsifiers are known W/O and also O/W emulsifiers, for example polyglycerol esters, sorbitan esters and partially esterified glycerides. Typical examples of fats are glycerides; waxes include beeswax, paraffin wax and microwaxes, if desired in combination with hydrophilic waxes. Suitable stabilizers are metal salts of fatty acids, for example magnesium stearate, aluminum stearate and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, furthermore fatty alcohols, monoglycerides and fatty acids, polyacrylates, polyvinyl alcohol and polyvinylpyrrolidone. The term biogenic active ingredients is taken to mean, for example, plant extracts, albamin hydrolysates and vitamin complexes. Customary film formers are, for example, hydrocolloids, such as chitosan, microcrystalline chitosan and quaternized chitosan, polyvinylpyrrolidone, vinylpyrrolidone-vinyl acetate copolymers, acrylic acid polymers, quaternary cellulose derivatives and similar compounds. Examples of suitable preservatives are formaldehyde solution, p-hydroxybenzoate and sorbic acid. Examples of suitable pearlescent agents are glycol distearic esters, such as ethylene glycol distearate, but also fatty acids and fatty acid monoglycol esters. Suitable colorants are the substances which are suitable and approved for cosmetic purposes, as listed, for example, in the publication "Kosmetische F ärbemittel" [Cosmetic Colorants] by the Farbstoffkommission der Deutschen Forschungsgemeinschaft, published by Verlag Chemie, Weinheim, 1984. These colorants are usually employed in concentrations of from 0.001 to 0.1% by weight, based on the total mixture.

In accordance with the invention, the preparations according to the invention advantageously comprise one or more antioxidants. Favorable, but nevertheless optional antioxidants are all natural, synthetic and/or partially synthetic antioxidants which are suitable or customary for cosmetic and/or dermatological applications.

The antioxidants are particularly advantageously selected from the group consisting of:

amino acids (for example glycine, histidine, tyrosine and tryptophan) and derivatives thereof, imidazoles (for example urocaninic acid) and derivatives thereof, peptides, such as D,L,-carnosine, D-carnosine, L-carnosine and derivatives thereof (for example anserine), carotenoids (for example β-carotene and lycopine) and derivatives thereof, lipoic acid and derivatives thereof (for example dihydrolipoic acid), aurothioglucose, propylthiouracil and other thio compounds (for example thioredoxin, glutathione, cystein, cystine, cystamine and the glycosyl, N-acetyl, methyl, ethyl, propyl, amyl, butyl, lauryl, palmitoyl, oleyl, γ-linoyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (for example buthionine sulfoximine, homocystein sulfoximine, buthionine sulfone, penta-, hexa- and heptathionine sulfoximine) in very small compatible dosages (for example pmol to μmol/kg), furthermore (metal) chelators (for example α-hydroxy fatty acids, palmitic acid, phytic acid and lactoferrin), α-hydroxy acids (for example citric acid, lactic acid and malic acid), humic acid, bile acid, bile extract, biliburin, biliverdin, EDTA, EGTA and derivatives thereof, unsaturated fatty acids and derivatives thereof (for example γ-linolenic acid, linoleic acid and oleic acid), folic acid and derivatives thereof, (for example 5-methyltetrahydrofolic acid), ubiquinone and ubiquinol and derivatives thereof, vitamin C and derivatives thereof (for example ascorbyl palmitate, ascorbyl phosphates and ascorbyl acetates), tocopherols and derivatives thereof (for example tocopheryl acetate and tocotrienol), vitamin A and derivatives (for example vitamin A palmitate), rutinic acid and derivatives thereof, ferulic acid and derivatives thereof, butylhydroxytoluene, butylhydroxyanisol, nordihydroguaiacic acid, nordihydroguairetic acid, trihydroxybutyrophenone, uric acid and derivatives thereof, stilbenes and derivatives thereof.

The total proportion of the auxiliaries and additives can be from 1 to 80% by weight, preferably from 6 to 40% by weight, and the non-aqueous component ("active substance") can be from to 80% by weight, preferably from 30 to 70% by weight, based on the preparation. The preparation can be prepared in a manner known per se, for example by hot, cold, hot-hot/cold or PIT emulsification. These are purely mechanical processes, with no chemical reaction.

Finally, further UV-absorbent substances known per se can also be used as long as they are stable in the overall system of the combination of UV filters to be used in accordance with the invention.

The majority of the light protection agents in the cosmetic and pharmaceutical preparations serving to protect the human epidermis consist of compounds which absorb UV light in the UV-3 region, i.e. in the region from 280 to 320 nm. For example, the proportion of cholesteric, liquid-crystalline compositions to be used in accordance with the invention is from 10 to 90% by weight, preferably from 20 to 70% by weight, based on the total amount of UV-B- and UV-A-absorbent substances.

Suitable UV filter substances which can be used in combination with the cholesteric, liquid-crystalline compositions used in accordance with the invention are any desired UV-A and UV-B filter substances. The following may be mentioned by way of example:

| No. | Substance | CAS No. (=acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2 oxobicyclo [2.2.1] heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |

-continued

| No. | Substance | CAS No. (=acid) |
|---|---|---|
| 12 | 2-Hydroxy-4-methoxybenzophenone-5-sulfonic acid (sulisobenzone) and its sodium salt | 4065-45-6 |
| 13 | 3-(4'-Methyl)benzylidenebornan-2-one | 36861-47-9 |
| 14 | 3-Benzylidenebornan-2-one | 15087-24-8 |
| 15 | 1-(4'-Isopropylphenyl)-3-phenylpropane-1,3-dione | 63250-25-9 |
| 16 | 4-Isopropylbenzyl salicylate | 94134-93-7 |
| 17 | 2,4,6-Trianilino(o-carbo-2'-ethylhexyl-1'-oxy)-1,3,5-triazine | 88122-99-0 |
| 18 | 3-Imidazol-4-yl-acrylic acid and its ethyl ester | 104-98-3 |
| 19 | Ethyl 2-cyano-3,3-diphenylacrylate | 5232-99-5 |
| 20 | 2'-Ethylhexyl 2-cyano-3,3-diphenylacrylate | 6197-30-4 |
| 21 | Menthyl-o-aminobenzoates (5-methyl-2-(1-methylethyl)-2-aminobenzoates) | 134-09-8 |
| 22 | Glyceryl p-aminobenzoate (1-glyceryl 4-aminobenzoate) | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (Mexonone) | 1641-17-4 |

preferably from 0.5 to 10% by weight, particularly preferably from 1 to 7% by weight. The respective formulations can be used, inter alia, for washing, coloring and styling hair.

The compositions to be used in accordance with the invention are generally distinguished by a particularly high reflection capacity in the region of UV-A and UV-B radiation with a sharp band structure. They car furthermore readily be incorporated into cosmetic and pharmaceutical formulations. In addition, they are particularly distinguished by their high photostability, and the preparations prepared therewith by their pleasant feel on the skin.

The UV filter action of the cholesteric, liquid-crystalline compositions a) and/or b) used in accordance with the invention can also be utilized for stabilization of active ingredients and auxiliaries in cosmetic and pharmaceutical formulations.

The examples below are intended to illustrate the novel use of the cholesteric, liquid-crystalline compositions in greater detail.

EXAMPLE 1

Preparation of cholesteric pigments (Pigment 1)

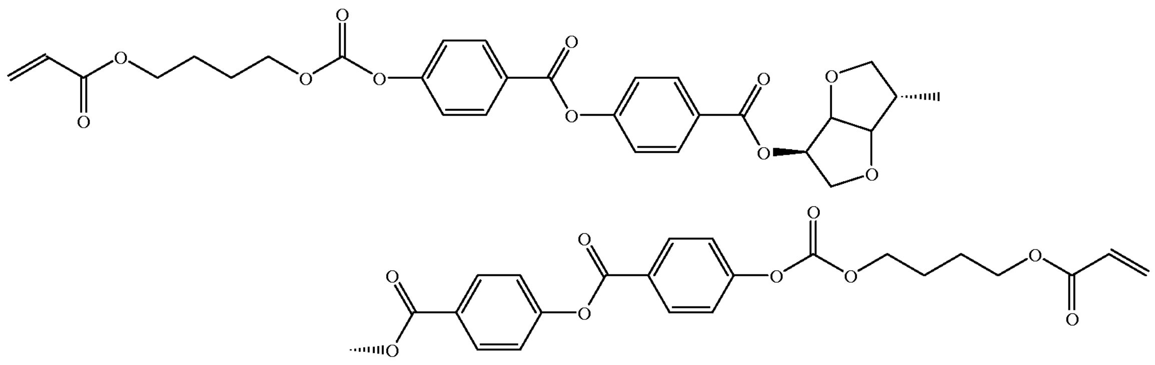

1

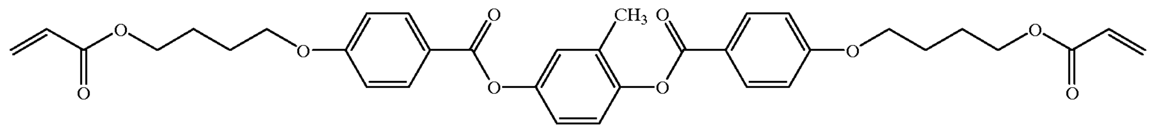

2

-continued

| No. | Substance | CAS No. (=acid) |
|---|---|---|
| 25 | Triethanolamine salicylate | 2174-16-5 |
| 26 | Dimethoxyphenylglyoxalic acid (sodium 3,4-dimethoxyphenylglyoxalate) | 4732-70-1 |
| 27 | 3-(4'-sulfo)benzylidenebornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |

Finally, mention should also be made of micronized pigments, such as titanium dioxide and zinc oxide.

For protection of human hair against UV rays, the cholesteric, liquid-crystalline compositions a) and/or b) used in accordance with the invention can be incorporated into shampoos, lotions, gels, hair sprays, aerosol foam creams or emulsions in concentrations of from 0.1 to 20% by weight, A cholesteric, liquid-crystalline mixture containing, as chiral monomer, a compound of the formula 1 given above and, as achiral, nematic monomer, a compound of the formula 2 given above was used. The undiluted cholesteric mixture comprised 94.8% by weight of the achiral, nematic compound, 5.2% by weight of the chiral compound and, as a photoinitiator, 2% by weight, based on the cholesteric, liquid-crystalline mixture, of 1-hydrocyclohexyl phenyl ketone, which is marketed under the name Irgacure 184. The mixture exhibited a $\lambda_{max}$ of 350 nm (T=70° C.).

To prepare the pigments, this mixture was dissolved in methyl ethyl ketone and, for the coating, applied to a polyethylene terephthalate film. The coating was carried out by the method described in DE-A 19 63 8797.

The thickness of the cholesteric layer was 2.5 μm. After the solvent had been evaporated at 70° C., the layer was crosslinked and cured by UV irradiation. The cured cholesteric layer obtained in this way was detached from the carrier and graded by grinding with subsequent screening. The size of the pigment particles was in the range <50 μm.

EXAMPLE 2

Preparation of cholesteric pigments (Pigment 2)

3
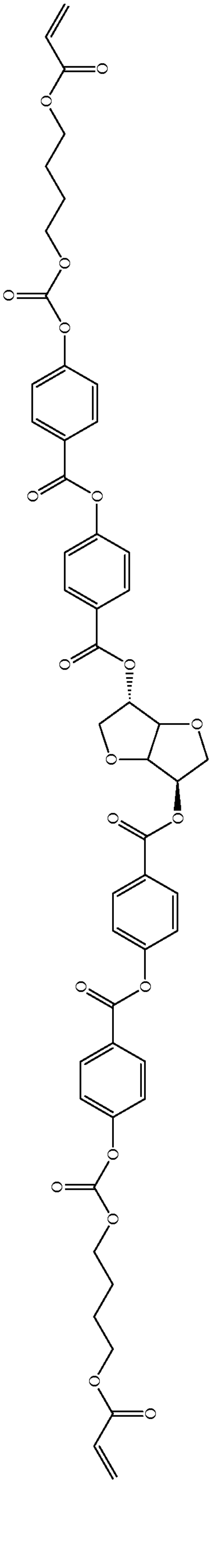
4
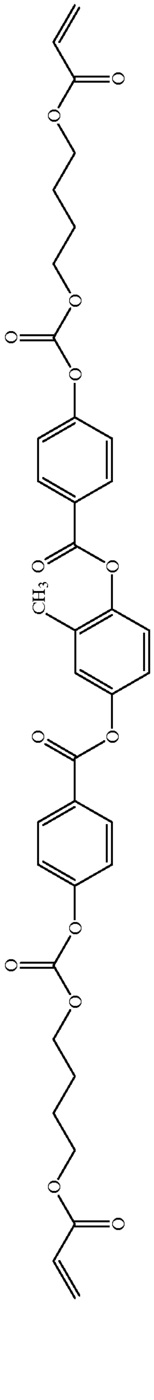

Pigments comprising, as chiral monomer, a compound of the formula 3 (5.2% by weight) and, as achiral, nematic monomer, the compound of the formula 4 (94.8% by weight) were prepared similarly to Example 1. The photoinitiator used was 2% by weight of Irgacure 184, based on the cholesteric, liquid-crystalline mixture. The mixture exhibited a $\lambda_{max}$ of 350 nm (T=23° C.).

EXAMPLE 3

Preparation of cholesteric pigments (Pigment 3)

5

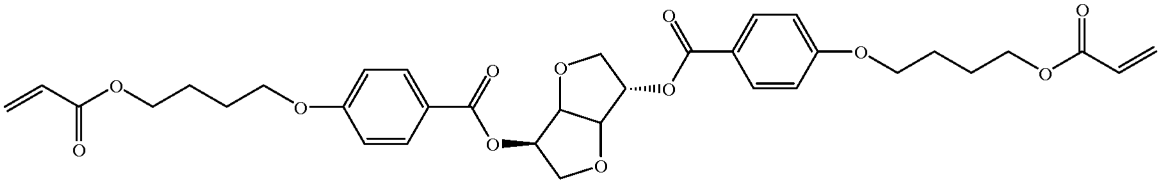

6

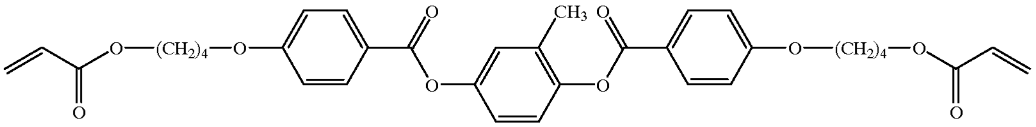

7

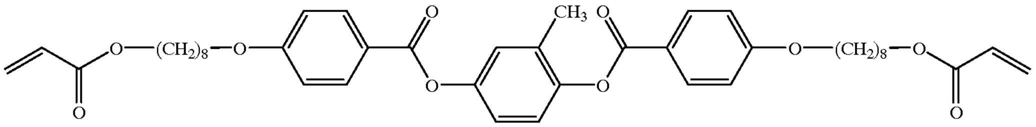

Pigments comprising, as chiral monomer, a compound of the formula 5 (11% by weight) and, as achiral, nematic monomer, a 1:1 mixture of the compounds of the formulae 6 and 7 (89% by weight) were prepared similarly to Example 1. The amount of the Irgacure 184 was 2% by weight, based on the cholesteric, liquid-crystalline mixture. The mixture exhibited a $\lambda_{max}$ of 355 nm (T=23° C.).

Preparations

EXAMPLE 4

Composition for lip care

Mass content (% by wt)

to 100 eucerinum anhydricum
10.00 glycerol
5.00 pigment 1
8.00 octyl methoxycinnamate
5.00 zinc oxide
4.00 castor oil
4.00 pentaerythrithyl stearate/caprate/caprylate adipate
3.00 glyceryl stearate SE
2.00 beeswax
0.50 tocopheryl acetate
2.00 microcrystalline wax
2.00 quaternium-18 bentonite
1.50 PEG-45/dodecyl glycol copolymer

EXAMPLE 5

Composition for lip care

Mass content (% by wt)

to 100 eucerinum anhydricum
10.00 glycerol
5.00 pigment 3
8.00 octyl methoxycinnamate
10.00 zinc oxide
4.00 castor oil
4.00 pentaerythrithyl stearate/caprate/caprylate adipate
3.00 glyceryl stearate SE
2.00 beeswax
0.50 tocopheryl acetate
2.00 microcrystalline wax
2.00 quaternium-18 bentonite
1.50 PEG-45/dodecyl glycol copolymer

EXAMPLE 6

Composition for sun block containing micropigments

Mass content (% by wt.)

to 100 water
10.00 octyl methoxycinnamate
6.00 PEG-7-hydrogenated castor oil
6.00 titanium dioxide
5.00 pigment 1
5.00 mineral oil
5.00 isoamyl p-methoxycinnamate
5.00 propylene glycol
3.00 jojoba oil
3.00 4-methylbenzylidene camphor
2.00 PEG-45/dodecyl glycol copolymer
1.00 dimethicon
0.50 PEG-40-hydrogenated castor oil
0.50 tocopheryl acetate
0.50 phenoxyethanol
0.20 EDTA

EXAMPLE 7

Composition for sun block containing micropigments

Mass content (% by wt.)

to 100 water
10.00 octyl methoxycinnamate
6.00 PEG-7-Hydrogenated castor oil
6.00 titanium dioxide
5.00 pigment 3
5.00 mineral oil
5.00 isoamyl p-methoxycinnamate
5.00 propylene glycol
3.00 jojoba oil
3.00 4-methylbenzylidene camphor
2.00 PEG-45/dodecyl glycol copolymer
1.00 dimethicon
0.50 PEG-40-hydrogenated castor oil
0.50 tocopheryl acetate
0.50 phenoxyethanol
0.20 EDTA

EXAMPLE 8

Fat-free gel
Mass content (% by wt.)
to 100 water
8.00 octyl methoxycinnamate
5.00 pigment 1
5.00 glycerol
5.00 PEG-25 PABA
1.00 4-methylbenzylidene camphor
0.40 acrylate C10–C30 alkyl acrylate crosspolymer
0.30 imidazolidinyl urea
0.25 hydroxyethyl cellulose
0.25 sodium methylparabene
0.20 disodium EDTA
0.15 fragrance
0.15 sodium propylparaben
0.10 sodium hydroxide

EXAMPLE 9

Fat-free gel
Mass content (% by wt.)
to 100 water
8.00 octyl methoxycinnamate
7.00 pigment 3
5.00 glycerol
5.00 PEG-PABA
1.00 4-methylbenzylidene camphor
0.40 acrylate C10–C30 alkyl acrylate crosspolymer
0.30 imidazolidinyl urea
0.25 hydroxyethyl cellulose
0.25 sodium methylparaben
0.20 disodium EDTA
0.15 fragrance
0.15 sodium propylparaben
0.10 sodium hydroxide

EXAMPLE 10

Sun cream (SPF 20)
Mass content (% by wt.)
to 100 water 8.00 octyl methoxycinnamate
6.00 PEG-7-hydrogenated castor oil
5.00 pigment 1
6.00 mineral oil
5.00 zinc oxide
5.00 isopropyl palmitate
5.00 imidazolidinyl urea
3.00 jojoba oil
2.00 PEG-45/dodecyl glycol copolymer
1.00 4-methylbenzylidene camphor
0.60 magnesium stearate
0.50 tocopheryl acetate
0.25 methylparaben
0.20 disodium EDTA
0.15 propylparaben

EXAMPLE 11

Sun cream (SPF 20)
Mass content (% by wt.)
to 100 water
10 8.00 octyl methoxycinnamate
6.00 PEG-7-hydrogenated castor oil
5.00 pigment 3
6.00 mineral oil
5.00 zinc oxide
5.00 isopropyl palmitate
5.00 imidazolidinyl urea
3.00 jojoba oil
2.00 PEG-45/dodecyl glycol copolymer
1.00 4-methylbenzylidene camphor
0.60 magnesium stearate
0.50 tocopheryl acetate
0.25 methylparaben
0.20 disodium EDTA
0.15 propylparaben

EXAMPLE 12

Water-resistant sun cream
Mass content (% by wt.)
to 100 water
8.00 octyl methoxycinnamate
5.00 PEG-7-hydrogenated castor oil
5.00 propylene glycol
4.00 isopropyl palmitate
4.00 caprylic/capric triglyceride
5.00 pigment 1
4.00 glycerol
3.00 jojoba oil
2.00 4-methylbenzylidene camphor
1.50 PEG-45/dodecyl glycol copolymer
1.50 dimethicon
0.70 magnesium sulfate
0.50 magnesium stearate
0.50 tocopheryl acetate
0.15 fragrance

EXAMPLE 13

Water-resistant sun cream
Mass content (% by wt.)

to 100 water
8.00 octyl methoxycinnamate
5.00 PEG-7-hydrogenated castor oil
5.00 propylene glycol
4.00 isopropyl palmitate
4.00 caprylic/capric triglyceride
5.00 pigment 3
4.00 glycerol
3.00 jojoba oil
2.00 4-methylbenzylidene camphor
1.50 PEG-45/dodecyl glycol copolymer
1.50 dimethicon
0.70 magnesium sulfate
0.50 magnesium stearate
0.50 tocopheryl acetate
0.15 fragrance

EXAMPLE 14

Sun milk (SPF 6)
Mass content (% by wt.)
to 100 water
10.00 mineral oil
6.00 PEG-7-hydrogenated castor oil
5.00 isopropyl palmitate
3.50 octyl methoxycinnamate
3.00 pigment 1
3.00 caprylic/capric triglyceride
3.00 jojoba oil
2.00 PEG-45/dodecyl glycol copolymer
0.70 magnesium sulfate
0.60 magnesium stearate
0.50 tocopheryl acetate
0.30 glycerol
0.25 methylparaben
0.15 propylparaben

EXAMPLE 15

Sun milk (SPF 6)
Mass content (% by wt.)
to 100 water
10.00 mineral oil
6.00 PEG-7-hydrogenated castor oil
5.00 isopropyl palmitate
3.50 octyl methoxycinnamate
3.00 pigment 3
3.00 caprylic/capric triglyceride
3.00 jojoba oil
2.00 PEG-45/dodecyl glycol copolymer
0.70 magnesium sulfate
0.60 magnesium stearate
0.50 tocopheryl acetate
0.30 glycerol
0.25 methylparaben
0.15 propylparaben

We claim:

1. A cholesteric liquid-crystalline composition comprising
a) at least one chiral, liquid-crystalline, polymerizable monomer of the formula I, $$[Z^1\text{-}Y^1\text{-}(A^1)_m\text{-}Y^2\text{-}M^1\text{-}Y^3\text{-}]_n\text{-}X \quad \text{I}$$

by means of which a cholesteric liquid-crystalline phase having a pitch of less than 450 nm can be obtained, where the variables, independently of one another, have the following meanings:

$A^1$ is a spacer having a chain length of from 1 to 30 carbon atoms, $Y^1$ to $Y^3$ are a chemical bond, —O—, —S—, —C(=O)—O—, —O—C(=O)—, —CH=CH—C(=O)—O—, —O—C(=O)—O—, —C(=O)—N(R)— or —(R)N—C(=O)—, —$CH_2$—O—, —O—$CH_2$—, —CH=N—, —N=CH— or —N=N—, $M^1$ is a mesogenic group, R is hydrogen or $C_1$–$C_4$-alkyl, $Z^1$ is hydrogen, $C_1$–$C_4$-alkyl, a polymerizable group or a radical carrying a polymerizable group, X is an n-valent chiral radical, m is 0 or 1, n is from 1 to 6, where the radicals $Z^1$, $Y^1$, $Y^2$, $Y^3$, $A^1$ and $M^1$ may be identical or different and at least one radical $Z^1$ is a polymerizable group or a radical containing a polymerizable group if n is greater than 1, or b) a mixture of $b_1$) at least one achiral, liquid-crystalline, polymerizable monomer of the formula II $$Z^2\text{-}Y^4\text{-}(A^2)_o\text{-}Y^5\text{-}M^2\text{-}Y^6\text{-}(A^3)_p\text{-}Y^7\text{-}Z^3 \quad \text{II}$$

where the variables, independently of one another, have the following meanings:

$A^2$ and $A^3$ are a spacer having a chain length of from 1 to 30 carbon atoms, $M^2$ is a mesogenic group, $Y^4$ to $Y^7$ are a chemical bond, —O—, —S—, —C(=O)—O—, —O—C(=O)—, —CH=CH—C(=O)—O—, —O—C(=O)—O—, —C(=O)—N($R^1$)— or —($R^1$)N—C(=O)—, —$CH_2$—O—, —O—$CH_2$—, —CH=N—, —N=CH— or —N=N—, $R^1$ is hydrogen or $C_1$–$C_4$-alkyl, o and p are 0 or 1

$Z^2$ and $Z^3$ are hydrogen, $C_1$–$C_4$-alkyl, a polymerizable group or a radical carrying a polymerizable group, where at least one of the variables $Z^2$ and $Z^3$ is a polymerizable group or a radical carrying a polymerizable group, and $b_2$) at least one chiral additive by means of which a cholesteric liquid-crystalline phase having a pitch of less than 450 nm can be obtained, as UV filters in cosmetic and pharmaceutical preparations for protecting the human skin or human hair against sunlight, alone or together with compounds which absorb in the UV region and are known for cosmetic and pharmaceutical preparations.

2. A cholesteric, liquid-crystalline composition as claimed in claim 1 in which the chiral additive $b_2$) is at least one chiral, polymerizable monomer of the formula III, $$[Z^1\text{-}Y^1\text{-}(A^1)_m\text{-}Y^2\text{-}M^3\text{-}Y^3\text{-}]_n\text{-}X \quad \text{III}$$

where $Z^1$, $Y^1$, $Y^2$, $Y^3$, $A^1$, X, m and n are as defined in claim 1, and $M^3$ is a divalent radical containing at least one heterocyclic or isocyclic ring system.

3. A cholesteric, liquid-crystalline composition as claimed in claim 1, where $A^1$ to $A^3$ are spacers having a chain length of from 1 to 6 carbon atoms;

$M^1$ to $M^3$ are radicals from the group consisting of:

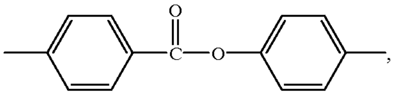,

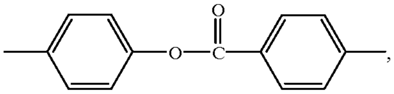,

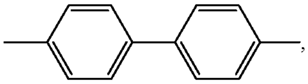,

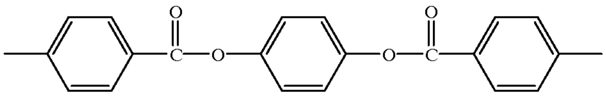 and

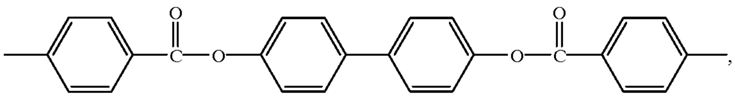, where each aromatic ring may carry up to three identical or different substituents from the following group:

hydrogen, $C_1$–$C_{20}$-alkyl, $C_1$–$C_{20}$-alkoxy, $C_1$–$C_{20}$-alkoxycarbonyl, N-$C_1$–$C_{20}$-alkylaminocarbonyl, $C_1$–$C_{20}$-alkylcarbonyl, $C_1$–$C_{20}$-alkylcarbonyloxy, N-$C_1$–$C_{20}$-alkylcarbonylamino, formyl, halogen, cyano, hydroxyl and nitro;

X is a chiral radical from the group consisting of:

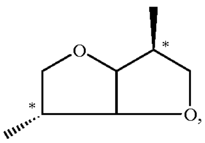, 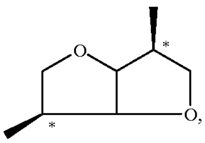,

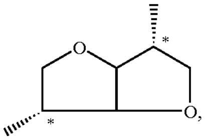, 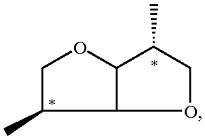, and

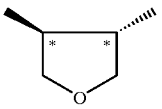 ;

n is 2, and o and p are 1.

4. A cholesteric, liquid-crystalline composition as claimed in claim 1 as photostable UV reflectors.

5. A cholesteric, liquid-crystalline composition as defined in claim 1 as UV stabilizers in cosmetic and pharmaceutical formulations.

6. A cholesteric, liquid-crystalline composition as claimed in claim 1 in the form of pigments.

7. A pigment comprising polymerized, cholesteric, liquid-crystalline compositions as claimed in claim 1.

8. A multilayer pigment as claimed in claim 7.

9. A cosmetic and/or pharmaceutical preparation containing a light stabilizer for protecting the human epidermis or human hair against UV light in the region from 280 to 400 nm, comprising cholesteric, liquid-crystalline compositions as claimed in claim 1 in effective amounts as photostable UV filters, in a cosmetically and/or pharmaceutically suitable carrier, alone or together with UV-absorbent compounds known for cosmetic and/or pharmaceutical preparations.

10. A cosmetic and/or pharmaceutical preparation as claimed in claim 9, wherein the UV filter is a cholesteric, liquid-crystalline composition.

11. A cosmetic and/or pharmaceutical preparation as claimed in claim 9, wherein the UV filter is a cholesteric, liquid-crystalline composition in the form of a pigment.

12. A cosmetic and/or pharmaceutical preparation as claimed in claim 9, wherein the UV filter is a cholesteric, liquid-crystalline composition in the form of a multilayer pigment.

* * * * *

UNITED STATES PATENT AND TRADEMARK OFFICE

CERTIFICATE OF CORRECTION

PATENT : 6,060,042

DATED : May 9, 2000

INVENTOR(S) : SCHUHMACHER et al.

It is certified that error appears in the above-identified patent and that said Letters Patent is hereby corrected as shown below:

Column 46, claim 9, line 41, after "known" insert --per se--.

Signed and Sealed this

Twentieth Day of March, 2001

Nicholas P. Godici

Attest:

NICHOLAS P. GODICI

*Attesting Officer*

*Acting Director of the United States Patent and Trademark Office*